(12) United States Patent
Lin et al.

(10) Patent No.: US 10,023,649 B2
(45) Date of Patent: Jul. 17, 2018

(54) METHOD OF TREATING CANCER WITH A COMBINATION OF AN ANTI-CCR4 ANTIBODY AND A 4-1BB AGONIST

(71) Applicants: Pfizer Inc., New York, NY (US); KYOWA HAKKO KIRIN CO., LTD., Tokyo (JP)

(72) Inventors: Chia-Yang Lin, London (GB); Shihao Chen, Foster City, CA (US); LiFen Lee, Palo Alto, CA (US); Shobha Potluri, Foster City, CA (US); Denis Healy, Princeton, NJ (US); Margaret Marshall, Princeton, NJ (US); Naoki Sawada, Tokyo (JP)

(73) Assignees: Pfizer Inc., New York, NY (US); Kyowa Hakko Kirin Co., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 15/312,515

(22) PCT Filed: May 15, 2015

(86) PCT No.: PCT/US2015/031081
§ 371 (c)(1),
(2) Date: Nov. 18, 2016

(87) PCT Pub. No.: WO2015/179236
PCT Pub. Date: Nov. 26, 2015

(65) Prior Publication Data
US 2017/0088627 A1    Mar. 30, 2017

Related U.S. Application Data

(60) Provisional application No. 62/001,534, filed on May 21, 2014.

(51) Int. Cl.
| C07K 16/30 | (2006.01) |
| A61K 39/395 | (2006.01) |
| A61K 47/18 | (2017.01) |
| A61K 47/26 | (2006.01) |
| A61K 47/12 | (2006.01) |
| A61K 39/00 | (2006.01) |

(52) U.S. Cl.
CPC ........ *C07K 16/30* (2013.01); *A61K 39/39558* (2013.01); *A61K 47/12* (2013.01); *A61K 47/183* (2013.01); *A61K 47/26* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *A61K 2039/505* (2013.01); *A61K 2039/545* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/732* (2013.01); *C07K 2317/75* (2013.01)

(58) Field of Classification Search
None
See application file for complete search history.

(56) References Cited

U.S. PATENT DOCUMENTS

| 7,504,104 B2 | 3/2009 | Shitara |
| 8,337,850 B2 | 12/2012 | Ahrens |
| 8,461,304 B2 * | 6/2013 | Cicortas Gunnarsson ....... C07K 16/2866 424/130.1 |
| 8,491,901 B2 | 7/2013 | Imai |
| 8,491,902 B2 | 7/2013 | Shitara |
| 2011/0171210 A1 | 7/2011 | Marasco |
| 2013/0078240 A1 | 3/2013 | Ahrens |

FOREIGN PATENT DOCUMENTS

WO    WO2006088447    *  8/2006    ............. C07K 16/00

OTHER PUBLICATIONS

Yonezawa et al. Boosting Cancer Immunotherapy with Anti-CD137 antibody therapy Clin. Cancer Res. 21, 3113-31120, 2015.*
Asahi et al., "Defucosylated anti-CCR4 monoclonal antibody exercises potent ADCC-mediated antitumor effect in the novel tumor-bearing humanized NOD/Shi-scid, IL-2Rĩ null mouse model," Cancer Immunology, Immunotherapy, 59(8):1195-1206 (2009).
Broll et al., "CD137 expression in tumor vessel walls. High correlation with malignant tumors," American Journal of Clinical Pathology, 115(4):543-549 (2001).
Chang et al., "Humanization of an anti-CCR4 antibody that kills cutaneous T-cell lymphoma cells and abrogates suppression by T-regulatory cells," Molecular Cancer Therapeutics, 11(11):2451-2461 (2012).
D'Ambrosio et al., "Selective up-regulation of chemokine receptors CCR4 and CCR8 upon activation of polarized human type 2 Th cells," Journal of Immunology, 161(10):5111-5115 (1998).
Houot et al., "Therapeutic effect of CD137 immunomodulation in lymphoma and its enhancement by Treg depletion," Blood, 114(16):3431-3438 (2009).
Ishida et al., "Defucosylated anti-CCR4 monoclonal antibody (KW-0761) for relapsed adult T-cell leukemia-lymphoma: a multicenter phase II study," Journal of Clinical Oncology, 30(8):837-842 (2012).
Kohrt et al, "CD137 stimulation enhances the antilymphoma activity of anti-CD20 antibodies," Blood, 117(8):2423-2432 (2011).
Lynch, "The promise of 4-1BB (CD137)-mediated immunomodulation and the immunotherapy of cancer," Immunological Reviews, 222:277-286 (2008).
Maeda et al., "Induction of molecular remission by using anti-CC-chemokine receptor 4 (anti-CCR4) antibodies for adult T-cell leukemia: a risk of opportunistic infection after treatment with anti-CCR4 antibodies," Retrovirology, 11(1):P15 (2014).

(Continued)

*Primary Examiner* — Elly-Gerald Stoica
(74) *Attorney, Agent, or Firm* — Arnold & Porter Kaye Scholer LLP

(57) ABSTRACT

The present disclosure describes combination therapies comprising an antibody which specifically binds to human CCR4 and a selective 4-1BB agonist, and the use of the combination therapies for the treatment of cancer.

24 Claims, 10 Drawing Sheets

(56) References Cited

OTHER PUBLICATIONS

Mariani et al., "Dominance of CCL22 over CCL17 in induction of chemokine receptor CCR4 desensitization and internalization on human Th2 cells," European Journal of Immunology, 34(2):231-240 (2004).

Meyer et al.,"Cloning and characterization of a novel murine macrophage inflammatory protein-1 alpha receptor," Journal of Biological Chemistry, 271(24):14445-14451 (1996).

Olofsson et al., "CD137 is expressed in human atherosclerosis and promotes development of plaque inflammation in hypercholesterolemic mice," Circulation, 117(10):1292 1301 (2008).

PCT International Search Report and Writtren Opinion for Application No. PCT/US2015/031081, dated Sep. 1, 2015 (13 pages).

Power et al., "Molecular cloning and functional expression of a novel CC chemokine receptor cDNA from a human basophilic cell line," Journal of Biological Chemistry, 270(33):19495-19500 (1995).

Sabbagh et al., "ERK-dependent Bim modulation downstream of the 4-1BB-TRAF1 signaling axis is a critical mediator of CD8 T cell survival in vivo," Journal of Immunolgy, 180(12):8093-8101 (2008).

Seaman et al., "Genes that distinguish physiological and pathological angiogenesis," Cancer Cell, 11(6):539-554 (2007).

Sugiyama et al., "Anti-CCR4 mAb selectively depletes effector-type FoxP3+CD4+ regulatory T cells, evoking antitumor immune responses in humans," PNAS, 110(44):17945-17950 (2003).

Taguchi et al., "Molecular analysis of loss of CCR4 expression during mogamulizumab monotherapy in an adult T cell leukemia/lymphoma patient," Annals of Hematology, 94(4):693-695 (2015).

Vinay et al., "Dual immunoregulatory pathways of 4-1BB signaling," Journal of Molecular Medicine, 84(9):726-736 (2006).

Wang et al., "Immune regulation by 4-1BB and 4-1BBL: complexities and challenges," Immunological Reviews, 229(1):192-215 (2009).

Yamamoto et al., "Phase I study of KW-0761, a defucosylated humanized anti-CCR4 antibody, in relapsed patients with adult T-cell leukemia-lymphoma and peripheral T-cell lymphoma," Journal of Clinical Oncology, 28(9):1591-1598 (2010).

Zhang et al., "CD137 promotes proliferation and survival of human B cells," Journal of Immunology, 184(2):787-795 (2010).

Communication pursuant to Article 94(3) EPC, issued in EP Appln. 15727159.4 (dated Feb. 1, 2018).

Fisher et al., "Targeting of 4-1BB by Monoclonal Antibody PF-05082566 Enhances T-Cell Function and Promotes Anti-Tumor Activity," *Cancer Immunol. Immunother.*, 61:1721-1733 (2012).

Kyowa Hakko, "Antineoplastic Agent Humanized Anti-CCR4 Monoclonal Antibody. Poteligeo® Injection. Mogamulizumab (Genetical Recombination) Drug Product," pp. 1-5 (2012).

Mitsui et al., "Two Distinct Mechanisms of Augmented Antitumor Activity by Modulation of Immunostimulatory/Inhibitory Signals," *Clin. Cancer Res.*, 16(10):2781-2791 (2010).

Pfizer and Kyowa Hakko Kirin Co., Ltd., "A Study of PF-05082566 in Combination with Mogamulizumab in Patients with Advanced Solid Tumors," Clinical Trial NCT02444793, https://clinicaltrials.gov/ct2/show/NCT02444793 (2015).

* cited by examiner

FIG 1

KW0761 light chain CDR1 (SEQ ID NO:1)

RSSRNIVHINGDTYLE

KW0761 light chain CDR2 (SEQ ID NO:2)

KVSNRFS

KW0761 light chain CDR3 (SEQ ID NO:3)

FQGSLLPWT

KW0761 heavy chain CDR1 (SEQ ID NO:4)

NYGMS

KW0761 heavy chain CDR2 (SEQ ID NO:5)

TISSASTYSYYPDSVKG

KW0761 heavy chain CDR3 (SEQ ID NO:6)

HSDGNFAFGY

FIG 2

Mab1567 light chain CDR1 (SEQ ID NO:7)
KSSQSILYSSNQKNYLA

Mab1567 light chain CDR2 (SEQ ID NO:8)
WASTRES

Mab1567 light chain CDR3 (SEQ ID NO:9)
HQYLSSYT

Mab1567 heavy chain CDR1 (SEQ ID NO:10)
GYTFASYY

Mab1567 heavy chain CDR2 (SEQ ID NO:11)
WINPGNVNTKYNEKFKG

Mab1567 heavy chain CDR3 (SEQ ID NO:12)
STYYRPLDY

FIG 3 huCCR4 heavy chain variable region (SEQ ID NO:13)

QVQLVQSGAEVKKPGASVKVSCKASGYTFASYYMHWMRQAPGQGLEWIGWINPGN
VNTKYNEKFKGRATLTVDTSTNTAYMELSSLRSEDTAVYYCARSTYYRPLDYWGQ
GTLVTVSS huCCR4 light chain variable region (SEQ ID NO:14)

DIVMTQSPDSLAVSLGERATINCKSSQSILYSSNQKNYLAWYQQKPGQSPKLLIY
WASTRESGVPDRFSGSGSGTDFTLTISSLQAEDVAVYYCHQYLSSYTFGQGTKLE
IK

FIG 4

KW-0761 Heavy chain (SEQ ID NO:15)

EVQLVESGGD LVQPGRSLRL SCAASGFIFS NYGMSWVRQA PGKGLEWVAT
ISSASTYSYY PDSVKGRFTI SRDNAKNSLY LQMNSLRVED TALYYCGRHS
DGNFAFGYWG QGTLVTVSSA STKGPSVFPL APSSKSTSGG TAALGCLVKD
YFPEPVTVSW NSGALTSGVH TFPAVLQSSG LYSLSSVVTV PSSSLGTQTY
ICNVNHKPSN TKVDKKVEPK SCDKTHTCPP CPAPELLGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSRDEL TKNQVSLTCL VKGFYPSDIA VEWESNGQPE NNYKTTPPVL
DSDGSFFLYS KLTVDKSRWQ QGNVFSCSVM HEALHNHYTQ KSLSLSPGK

KW-0761 Light chain (SEQ ID NO: 16)

DVLMTQSPLS LPVTPGEPAS ISCRSSRNIV HINGDTYLEW YLQKPGQSPQ
LLIYKVSNRF SGVPDRFSGS GSGTDFTLKI SRVEAEDVGV YYCFQGSLLP
WTFGQGTKVE IKRTVAAPSV FIFPPSDEQL KSGTASVVCL LNNFYPREAK
VQWKVDNALQ SGNSQESVTE QDSKDSTYSL SSTLTLSKAD YEKHKVYACE
VTHQGLSSPV TKSFNRGEC

KW-0761 Heavy chain variable region (SEQ ID NO: 17)

EVQLVESGGD LVQPGRSLRL SCAASGFIFS NYGMSWVRQA PGKGLEWVAT
ISSASTYSYY PDSVKGRFTI SRDNAKNSLY LQMNSLRVED TALYYCGRHS
DGNFAFGYWG QGTLVTVSS

KW-0761 Light chain variable region (SEQ ID NO: 18)

DVLMTQSPLS LPVTPGEPAS ISCRSSRNIV HINGDTYLEW YLQKPGQSPQ
LLIYKVSNRF SGVPDRFSGS GSGTDFTLKI SRVEAEDVGV YYCFQGSLLP
WTFGQGTKVE IK

FIG 5

Nivolumab

Heavy chain (SEQ ID NO: 23)

```
QVQLVESGGG VVQPGRSLRL DCKASGITFS NSGMHWVRQA PGKGLEWVAV  50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK            440
```

Light chain (SEQ ID NO: 24)

```
EIVLTQSPAT LSLSPGERAT LSCRASQSVS SYLAWYQQKP GQAPRLLIYD  50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                        214
```

FIG 6

Heavy chain variable region for the 4-1BB antibody (SEQ ID NO: 19)

EVQLVQSGAEVKKPGESLRISCKGSGYSFSTYWISWVRQMPGKGLEWM
GKIYPGDSYTNYSPSFQGQVTISADKSISTAYLQWSSLKASDTAMYYC
ARGYGIFDYWGQGTLVTVSS

Light chain variable region for the 4-1BB antibody (SEQ ID NO: 20)

SYELTQPPSVSVSPGQTASITCSGDNIGDQYAHWYQQKPGQSPVLVIY
QDKNRPSGIPERFSGSNSGNTATLTISGTQAMDEADYYCATYTGFGSL
AVFGGGTKLTVL

FIG 7

Amino Acid Sequence of Human 4-1BB (SEQ ID No: 26)
Mgnscynivatlllvlnfertrslqdpcsncpagtfcdnnrnqicspcppnsfss
aggqrtcdicrqckgvfrtrkecsstsnaecdctpgfhclgagcsmceqdckqgq
eltkkgckdccfgtfndqkrgicrpwtncsldgksvlvngtkerdvvcgpspadl
spgassvtppaparepghspqiisfflaltstallfllffltlrfsvvkrgrkkl
lyifkqpfmrpvqttqeedgcscrfpeeeeggcel

Heavy chain CDR1 for 4-1BB (SEQ ID No: 27)
STYWIS

Heavy chain CDR2 for 4-1BB (SEQ ID No: 28)
KIYPGDSYTNYSPSFQG

Heavy chain CDR3 for 4-1BB (SEQ ID No: 29)
RGYGIFDY

Light chain CDR1 for 4-1BB (SEQ ID No: 30)
SGDNIGDQYAH

Light chain CDR2 for 4-1BB (SEQ ID No: 31)
QDKNRPS

Light chain CDR3 for 4-1BB (SEQ ID No: 32)
ATYTGFGSLAV

FIG 8

4-1BB agonist antibody heavy chain (SEQ ID NO: 21)
EVQLVQSGAEVKKPGESLRISCKGSGYSFSTYWISWVRQMPGKGLEWMGKIYPGD
SYTNYSPSFQGQVTISADKSISTAYLQWSSLKASDTAMYYCARGYGIFDYWGQGT
LVTVSSastkgpsvfplapcsrstsestaalgclvkdyfpepvtvswnsgaltsg
vhtfpavlqssglyslssvvtvpssnfgtqtytcnvdhkpsntkvdktverkccv
ecppcpappvagpsvflfppkpkdtlmisrtpevtcvvvdvshedpevqfnwyvd
gvevhnaktkpreeqfnstfrvvsvltvvhqdwlngkeykckvsnkglpapiekt
isktkgqprepqvytlppsreemtknqvsltclvkgfypsdiavewesngqpenn
ykttppmldsdgsfflyskltvdksrwqqgnvfscsvmhealhnhytqkslslsp
gk

4-1BB agonist antibody light chain (SEQ ID NO: 22)
SYELTQPPSVSVSPGQTASITCSGDNIGDQYAHWYQQKPGQSPVLVIYQDKNRPS
GIPERFSGSNSGNTATLTISGTQAMDEADYYCATYTGFGSLAVFGGGTKLTVLgq
pkaapsvtlfppsseelqankatlvclisdfypgavtvawkadsspvkagvettt
pskqsnnkyaassylsltpeqwkshrsyscqvthegstvektvaptecs

SEQUENCE LISTING

<160> NUMBER OF SEQ ID NOS: 32

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Arg Ser Ser Arg Asn Ile Val His Ile Asn Gly Asp Thr Tyr Leu Glu
1               5                   10                  15

<210> SEQ ID NO 2

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Phe Gln Gly Ser Leu Leu Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Asn Tyr Gly Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Thr Ile Ser Ser Ala Ser Thr Tyr Ser Tyr Tyr Pro Asp Ser Val Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

His Ser Asp Gly Asn Phe Ala Phe Gly Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Lys Ser Ser Gln Ser Ile Leu Tyr Ser Ser Asn Gln Lys Asn Tyr Leu
1               5                   10                  15

Ala
```

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Trp Ala Ser Thr Arg Glu Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

His Gln Tyr Leu Ser Ser Tyr Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Gly Tyr Thr Phe Ala Ser Tyr Tyr
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Trp Ile Asn Pro Gly Asn Val Asn Thr Lys Tyr Asn Glu Lys Phe Lys
1               5                   10                  15

Gly

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Ser Thr Tyr Tyr Arg Pro Leu Asp Tyr
1               5

<210> SEQ ID NO 13
<211> LENGTH: 118
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Ala Ser Tyr
                20                  25                  30

Tyr Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
        50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
                100                 105                 110

Leu Val Thr Val Ser Ser
            115
```

<210> SEQ ID NO 14
<211> LENGTH: 112
<212> TYPE: PRT
<213> ORGANISM: Artificial Sequence
<220> FEATURE:
<223> OTHER INFORMATION: Synthetic Construct

<400> SEQUENCE: 14

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
                100                 105                 110
```

<210> SEQ ID NO 15
<211> LENGTH: 449
<212> TYPE: PRT
<213> ORGANISM: Artificial Sequence
<220> FEATURE:
<223> OTHER INFORMATION: Synthetic Construct

<400> SEQUENCE: 15

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Ile Phe Ser Asn Tyr
                20                  25                  30

Gly Met Ser Trp Val Arg Gln Ala Pro Gly Lys Gly Leu Glu Trp Val
            35                  40                  45

Ala Thr Ile Ser Ser Ala Ser Thr Tyr Ser Tyr Tyr Pro Asp Ser Val
        50                  55                  60

Lys Gly Arg Phe Thr Ile Ser Arg Asp Asn Ala Lys Asn Ser Leu Tyr
65                  70                  75                  80
```

-continued

```
Leu Gln Met Asn Ser Leu Arg Val Glu Asp Thr Ala Leu Tyr Tyr Cys
                 85                  90                  95

Gly Arg His Ser Asp Gly Asn Phe Ala Phe Gly Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 16
<211> LENGTH: 219
<212> TYPE: PRT
<213> ORGANISM: Artificial Sequence
<220> FEATURE:
<223> OTHER INFORMATION: Synthetic Construct

<400> SEQUENCE: 16

Asp Val Leu Met Thr Gln Ser Pro Leu Ser Leu Pro Val Thr Pro Gly
1               5                   10                  15

Glu Pro Ala Ser Ile Ser Cys Arg Ser Ser Arg Asn Ile Val His Ile
            20                  25                  30

Asn Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 17
<211> LENGTH: 119
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Ile Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Ser Ala Ser Thr Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Gly Arg His Ser Asp Gly Asn Phe Ala Phe Gly Tyr Trp Gly Gln Gly
            100                 105                 110

Thr Leu Val Thr Val Ser Ser
        115

```
<210> SEQ ID NO 18
<211> LENGTH: 112
<212> TYPE: PRT
<213> ORGANISM: Artificial Sequence
<220> FEATURE:
<223> OTHER INFORMATION: Synthetic Construct

<400> SEQUENCE: 18

Asp Val Leu Met Thr Gln Ser Pro Leu Ser Leu Pro Val Thr Pro Gly
1               5                   10                  15

Glu Pro Ala Ser Ile Ser Cys Arg Ser Ser Arg Asn Ile Val His Ile
            20                  25                  30

Asn Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Leu Pro Trp Thr Phe Gly Gln Gly Thr Lys Val Glu Ile Lys
            100                 105                 110

<210> SEQ ID NO 19
<211> LENGTH: 116
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 20
<211> LENGTH: 108
<212> TYPE: PRT
<213> ORGANISM: Artificial Sequence
<220> FEATURE:
<223> OTHER INFORMATION: Synthetic Construct

<400> SEQUENCE: 20

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30
```

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 21
<211> LENGTH: 442
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

```
Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

Ala Pro Thr Glu Cys Ser
        210

<210> SEQ ID NO 23
<211> LENGTH: 440
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 24
<211> LENGTH: 214
<212> TYPE: PRT
<213> ORGANISM: Artificial Sequence
<220> FEATURE:
<223> OTHER INFORMATION: Synthetic Construct

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 360
<212> TYPE: PRT
<213> ORGANISM: homo sapiens

<400> SEQUENCE: 25

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360

<210> SEQ ID NO 26
<211> LENGTH: 255
<212> TYPE: PRT
<213> ORGANISM: homo sapiens

<400> SEQUENCE: 26

Met Gly Asn Ser Cys Tyr Asn Ile Val Ala Thr Leu Leu Leu Val Leu
1               5                   10                  15

```
Asn Phe Glu Arg Thr Arg Ser Leu Gln Asp Pro Cys Ser Asn Cys Pro
                 20                  25                  30

Ala Gly Thr Phe Cys Asp Asn Arg Asn Gln Ile Cys Ser Pro Cys
             35                  40                  45

Pro Pro Asn Ser Phe Ser Ala Gly Gly Arg Thr Cys Asp Ile
 50                  55                  60

Cys Arg Gln Cys Lys Gly Val Phe Arg Thr Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
                130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Ser Thr Tyr Trp Ile Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Lys Ile Tyr Pro Gly Asp Ser Tyr Thr Asn Tyr Ser Pro Ser Phe Gln
1               5                  10                  15

Gly

<210> SEQ ID NO 29
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 29

Arg Gly Tyr Gly Ile Phe Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Ser Gly Asp Asn Ile Gly Asp Gln Tyr Ala His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Gln Asp Lys Asn Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Ala Thr Tyr Thr Gly Phe Gly Ser Leu Ala Val
1               5                   10
```

US 10,023,649 B2

METHOD OF TREATING CANCER WITH A COMBINATION OF AN ANTI-CCR4 ANTIBODY AND A 4-1BB AGONIST

CROSS-REFERENCE TO RELATED APPLICATIONS

This application is a United States National Stage under 35 U.S.C. § 371 of International Application No. PCT/US15/31081, filed May 15, 2015 (pending), which claims the benefit of U.S. provisional application No. 62/001,534 filed May 21, 2014, which are incorporated by reference in their entireties.

SEQUENCE LISTING

The instant application contains a Sequence Listing which has been submitted electronically in ASCII format and is hereby incorporated by reference in its entirety. Said ASCII copy, created on Nov. 18, 2016, is named PCFC-986-301-SL.txt and is 33520 bytes in size.

FIELD OF THE INVENTION

The present invention relates to combination therapies useful for the treatment of cancer. In particular, the invention relates to a combination therapy which comprises an antibody which specifically binds to human CC chemokine receptor 4 (CCR4) and an agonist of a 4-1BB protein.

BACKGROUND OF THE INVENTION

Chemokines have been recognized as a critical component of basal leukocyte trafficking essential for normal immune surveillance and response, as well as for several other functions in hematopoiesis, angiogenesis, control of viral infection, and T cell differentiation (Baggiolini et al., Ann. Rev. Immunol. 15:675 (1997); Zou et al., Nature 393:595 (1998); Tachibana et al., Nature 393:591 (1998)). This diverse array of biological activities, including mediation of a range of pro-inflammatory effects on leukocytes, such as triggering of chemotaxis, degranulation, synthesis of lipid mediators, and integrin activation, together with their critical role in the initiation and maintenance of inflammatory diseases, have made chemokines and chemokine receptors an attractive new set of therapeutic targets.

Chemokine receptor 4 (CCR4) was identified by Power et al. (J. Biol. Chem. 270:19495-19500 (1995); Genbank accession number X85740) and Meyer et al. (J. Biol. Chem. 271(24):14445-14451 (1996); Genbank accession number X94151). CCR4 is a seven-transmembrane G-protein coupled receptor and selectively expressed on Th2 cells and regulatory T cells (D'Ambrosio, et al. J. Immunol. 161: 5111-5115 (1998)). CCR4 expression on normal cells such as Th2 cells can be partly regulated by the ligand, especially macrophage-derived chemokine (MDC) (Mariani et al., Eur. J. Immunol. 34:231-240 (2004)), while the regulation by the ligands on cancer cells is not yet understood. It has been shown that anti-CCR4 monoclonal antibody selectively depletes effector-type FoxP3$^+$CD4$^+$ regulatory T cells, evoking antitumor immune responses in humans (Sugiyama et al., Proc. Nat. Acad. Sci. 110(44):17945-17950 (2003)).

KW-0761 (mogamulizumab or POTELIGEO™) is approved in Japan for relapsed or refractory CCR4-positive adult T-cell leukemia/lymphoma and relapsed or refractory CCR4-positive peripheral T-cell lymphoma (PTCL) and cutaneous T-cell lymphoma (CTCL). KW-0761 is a humanized monoclonal antibody of the immunoglobulin G, subclass 1 (IgG1) kappa isotype that targets CCR4 expressing cells and has shown an ability to deplete T-lymphocytes expressing CCR4 via ADCC. KW-0761 has enhanced ADCC activity due to defucosylation from the complex-type oligosaccharide at the constant (Fc) region. (Ishii et al., Clinical Cancer Research 16: 1520-31 (2010); Shitara et al., Human CDR-grafted antibody and antibody fragment thereof, U.S. Pat. No. 7,504,104; U.S. Pat. No. 8,491,901).

4-1BB (CD137 and TNFRSF9), which was first identified as an inducible costimulatory receptor expressed on activated T cells, is a membrane spanning glycoprotein of the Tumor Necrosis Factor (TNF) receptor superfamily. Current understanding of 4-1BB indicates that expression is generally activation dependent and encompasses a broad subset of immune cells including activated NK and NKT cells, regulatory T cells, dendritic cells (DC) including follicular DC, stimulated mast cells, differentiating myeloid cells, monocytes, neutrophils, eosinophils (Wang et al., Immunol Rev. 229(1):192-215 (2009)), and activated B cells (Zhang et al., J Immunol. 184(2):787-795 (2010)). 4-1BB expression has also been demonstrated on tumor vasculature (Broll K et al., Am J Clin Pathol. 115(4):543-549 (2001); Seaman et al., Cancer Cell 11(6):539-554 (2007)) and atherosclerotic endothelium (Olofsson et al., Circulation 117(10):1292 1301 (2008)). The ligand that stimulates 4-1BB (4-1BBL) is expressed on activated antigen-presenting cells (APCs), myeloid progenitor cells and hematopoeitic stem cells.

Interaction of 4-1BB on activated normal human B cells with its ligand at the time of B cell receptor engagement stimulates proliferation and enhances survival (Zhang et al., J Immunol. 184(2):787-795 (2010)). The potential impact of 4-1BB engagement in B cell lymphoma has been investigated in two published studies. Evaluation of several types of human primary NHL samples indicated that 4-1BB was expressed predominantly on infiltrating T cells rather than the lymphoma cells (Houot et al., Blood 114(16):3431-3438 (2009)). The addition of 4-1BB agonists to in vitro cultures of B lymphoma cells with rituximab and NK cells resulted in increased lymphoma killing (Kohrt et al., Blood 117(8): 2423-2432 (2011)). In addition, B cell immunophenotyping was performed in two experiments using PF-05082566 (anti-4-1BB agonist monoclonal antibody) in cynomolgus monkeys with doses from 0.001-100 mg/kg; in these experiments peripheral blood B cell numbers were either unchanged or decreased.

4-1BB is undetectable on the surface of naive T cells but expression increases upon activation. Upon 4-1BB activation, TRAF-1 and TRAF-2, which are pro-survival members of the TNFR-associated factor (TRAF) family, are recruited to the 4-1BB cytoplasmic tail, resulting in downstream activation of NFκB and the Mitogen Activated Protein (MAP) Kinase cascade including ERK, JNK, and p38 MAP kinases. NFkB activation leads to upregulation of Bfl-1 and Bcl-XL, pro-survival members of the Bcl-2 family. The pro-apoptotic protein Bim is downregulated in a TRAF-1 and ERK dependent manner (Sabbagh et al., J Immunol. 180(12):8093-8101 (2008)).

Reports have shown that 4-1BB agonist mAbs increase costimulatory molecule expression and markedly enhance cytolytic T lymphocyte responses, resulting in anti-tumor efficacy in various models. 4-1BB agonist mAbs have demonstrated efficacy in prophylactic and therapeutic settings for both monotherapy and combination therapy and have established durable anti-tumor protective T cell memory responses (Lynch et al., Immunol Rev. 222:277-286 (2008)).

4-1BB agonists also inhibit autoimmune reactions in a variety of autoimmunity models (Vinay et al., J Mol Med 84(9):726-736 (2006)).

SUMMARY

Methods for treating a cancer in an individual are provided herein. In some embodiments, the method comprises administering to the individual an anti-CCR4 antibody and a 4-1BB agonist.

Medicaments are also provided. In some embodiments, the medicament comprises an anti-CCR4 antibody for use in combination with a 4-1BB agonist for treating a cancer. In other embodiments, the medicament comprises a 4-1BB agonist for use in combination with an anti-CCR4 antibody for treating a cancer.

Other embodiments provide for use of an anti-CCR4 antibody in the manufacture of medicament for treating a cancer in an individual when administered in combination with a 4-1BB agonist and use of a 4-1BB agonist in the manufacture of a medicament for treating a cancer in an individual when administered in combination with an anti-CCR4 antibody.

Other embodiments provide for use of an anti-CCR4 antibody and a 4-1BB agonist in the manufacture of medicaments for treating a cancer in an individual. In some embodiments, the medicaments comprise a kit, and the kit also comprises a package insert comprising instructions for using the anti-CCR4 antibody in combination with a 4-1BB agonist to treat a cancer in an individual.

In some embodiments, the method comprises administering to the individual a combination therapy that comprises an agent that depletes $CD4^+$ T cells, and a 4-1BB agonist. In some embodiments, the $CD4^+$ T cells are $FoxP3^+CD4^+$ regulatory T cells. In some embodiments, the agent that depletes $CD4^+$ T cells selectively depletes $FoxP3^+CD4^+$ regulatory T cells. In some embodiments, the method comprises administering to the individual a combination therapy that comprises an agent that depletes $CD4^+$ T cells, a 4-1BB agonist, and a PD-1 antagonist. In some embodiments, the agent that depletes $CD4^+$ T cells is an anti-CCR4 antibody or an anti-CD4 antibody.

In some embodiments, the method comprises administering to the individual a combination therapy that comprises an anti-CCR4 antibody, a 4-1BB agonist, and a PD-1 antagonist. In some embodiments, the method comprises administering to the individual a combination therapy that comprises an anti-CD4 antibody, a 4-1BB agonist, and a PD-1 antagonist. In some embodiments, the PD-1 antagonist inhibits the binding of PD-L1 to PD-1. In some embodiments, the PD-1 antagonist also inhibits the binding of PD-L2 to PD-1. In some embodiments of the above treatment method, medicaments and uses, the PD-1 antagonist is a monoclonal antibody, or an antigen binding fragment thereof, that specifically binds to PD-1 or to PD-L1 and blocks the binding of PD-L1 to PD-1.

The combination therapy may also comprise one or more additional therapeutic agents. The additional therapeutic agent may be, e.g., a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, PD-1, TIM-3, LAG-3, GITR, CD137, ICOS, CD28, CD27, HVEM, BTLA, VISTA, CCR8, TIGIT, CD4, ARHGEF6, IKZF1, PTPRC, DOCK2, CCR4, CCR5, IL21R, IL2RB, NCKAP1L, SLAMF1, ITGAL, IL10RA, P2RY10, IL2RA, FMNL1, DOCK10, ITK, SASH3, KIAA0748, LCP2, TNFRSF9 (4-1BB, CD137), CYBB, and CTLA4), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

In some embodiments, the anti-CCR4 antibody specifically binds human CCR4. In some embodiments, the anti-CCR4 antibody can selectively deplete $CD4^+$ T cells. In some embodiments, the anti-CCR4 antibody may comprise a heavy chain and a light chain, wherein the heavy and light chains comprise the amino acid sequences shown in FIG. 4 (SEQ ID NO: 15 and SEQ ID NO: 16), with the proviso that the C-terminal lysine residue of SEQ ID NO: 15 is optionally absent.

In all of the above embodiments of the treatment method, medicaments and uses, the 4-1BB agonist binds to the extracellular domain of 4-1BB and is capable of agonizing 4-1BB. In some embodiments of the above treatment method, medicaments and uses, the 4-1BB agonist is a monoclonal antibody, or an antigen binding fragment thereof.

In some embodiments, the isolated antibody binds human 4-1BB at an epitope located within amino acid residues 115-156 of SEQ ID NO: 26. In some embodiments, the antibody comprises the H-CDR1 amino acid sequence of SEQ ID NO: 27, H-CDR2 amino acid sequence of SEQ ID NO: 28 and H-CDR3 amino acid sequence of SEQ ID NO: 29. In some embodiments, the 4-1BB agonist is a monoclonal antibody, or antigen-binding fragment thereof, that comprises the L-CDR1 amino acid sequence of SEQ ID NO: 30, L-CDR2 amino acid sequence of SEQ ID NO: 31, and L-CDR3 amino acid sequence of SEQ ID NO: 32.

In some embodiments, the 4-1BB agonist is a monoclonal antibody, or antigen-binding fragment thereof, that comprises a heavy chain variable region amino acid sequence as set forth in SEQ ID NO: 19.

In some embodiments, the 4-1BB agonist is a monoclonal antibody, or antigen-binding fragment thereof, that comprises a light chain variable region amino acid sequence as set forth in SEQ ID NO: 20.

In some embodiments, the 4-1BB agonist is a monoclonal antibody, or antigen-binding fragment thereof, that comprises a heavy chain variable region amino acid sequence as set forth in SEQ ID NO: 19, and further comprises a light chain variable region amino acid sequence as set forth in SEQ ID NO: 20.

In some embodiments, the 4-1BB agonist is a monoclonal antibody, or antigen-binding fragment thereof, that comprises a heavy chain amino acid sequence as set forth in SEQ ID NO: 21 and further comprises a light chain amino acid sequence as set forth in SEQ ID NO: 22, with the proviso that the C-terminal lysine residue of SEQ ID NO: 21 is optionally absent.

In some embodiments of the above treatment method, medicaments and uses of the invention, the individual is a human and the cancer is a solid tumor and in some embodiments, the solid tumor is bladder cancer, breast cancer, clear cell kidney cancer, colon cancer, head/neck squamous cell carcinoma, rectal cancer, lung squamous cell carcinoma, thyroid cancer, bladder cancer, cervical cancer, uterine cancer, endometrial cancer, lung adenocarcinoma, ovarian cancer, papillary kidney cancer, malignant melanoma, non-small-cell lung cancer (NSCLC), ovarian cancer, pancreatic cancer, prostate cancer, renal cell cancer, small-cell lung cancer (SCLC) or triple negative breast cancer. In some embodiments, the cancer is an advanced solid tumor malignancy.

In other embodiments of the above treatment method, medicaments and uses of the invention, the individual is a human and the cancer is a Heme malignancy and in some embodiments, the Heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

In some embodiments of any of the above treatment methods, medicaments and uses, the cancer tests positive for the expression of CCR4. In some embodiments, the cancer has elevated CCR4 expression.

In some embodiments of any the above treatment methods, medicaments and uses, the individual is a human and the cancer is an advanced solid tumor that tests positive for human CCR4.

BRIEF DESCRIPTION OF THE DRAWINGS

FIG. 1 depicts amino acid sequences of the light chain and heavy chain CDRs for an exemplary anti-CCR4 monoclonal antibody useful in the present invention (SEQ ID NOs:1-6).

FIG. 2 depicts amino acid sequences of the light chain and heavy chain CDRs for another exemplary anti-CCR4 monoclonal antibody useful in the present invention (SEQ ID NOs:7-12).

FIG. 3 depicts amino acid sequences of the heavy chain variable region and light chain variable region for an exemplary anti-CCR4 monoclonal antibody useful in the present invention (SEQ ID NO: 13 and SEQ ID NO: 14).

FIG. 4 depicts amino acid sequences of the full-length heavy and light chains for anti-CCR4 monoclonal antibody KW-0761 (SEQ ID NOs: 15 and 16, respectively), and the amino acid sequences of the heavy and light chain variable regions for anti-CCR4 monoclonal antibody KW-0761 (SEQ ID NOs: 17 and 18, respectively).

FIG. 5 depicts amino acid sequences of the heavy and light chains for anti-PD-1 antibody nivolumab (SEQ ID NOs: 23 and 24, respectively).

FIG. 6 depicts amino acid sequences of the heavy chain and light chain variable regions for the 4-1BB agonist antibody (SEQ ID NOs: 19 and 20, respectively).

FIG. 7 depicts amino acid sequences of the heavy chain CDR sequences (SEQ ID NOs: 27, 28, and 29), and light chain CDR sequences (SEQ ID NOs: 30, 31, and 32) for the 4-1BB agonist antibody.

FIG. 8 depicts amino acid sequences of the heavy and light chains for PF-05082566 (SEQ ID NOs. 21 and 22, respectively).

DETAILED DESCRIPTION

Abbreviations

Figure 9:
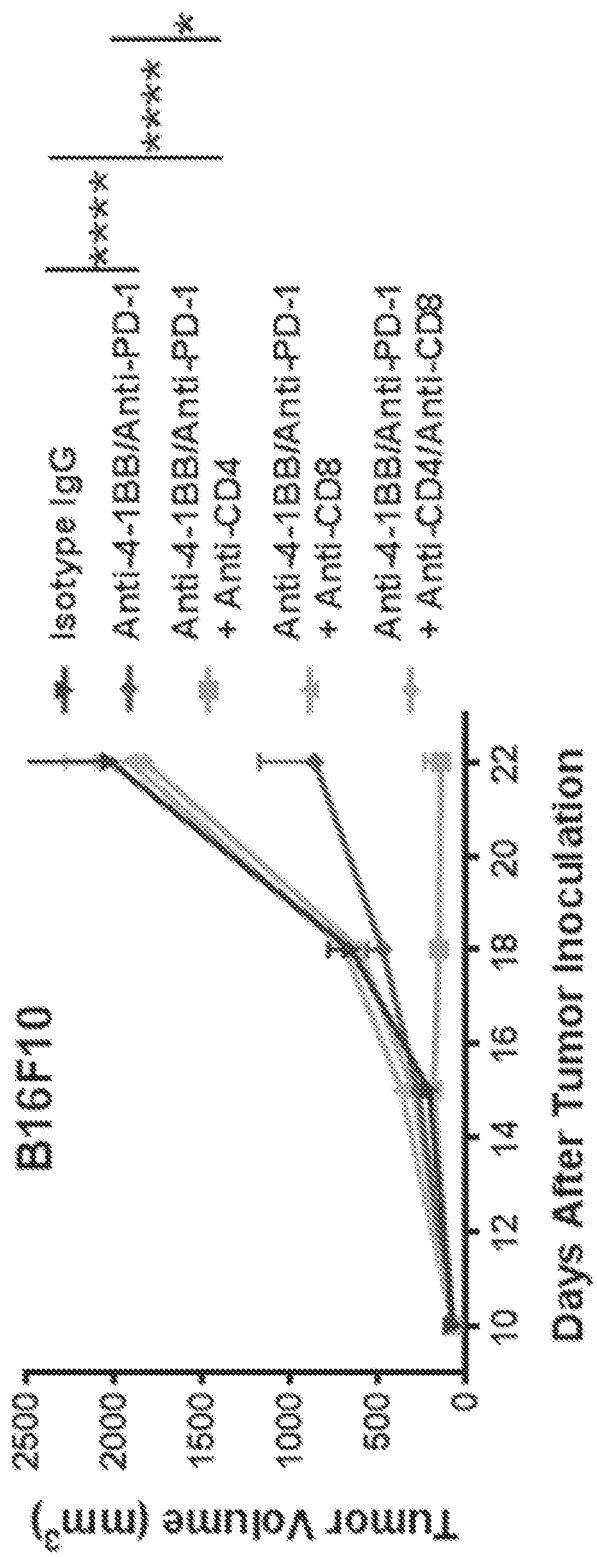
FIG. 9 depicts a graph showing the effect of CD4+ T cell depletion on 4-1BB agonist antibody treatment, PD-1 antagonist antibody treatment, and combination treatment in a B16 melanoma model.

Throughout the detailed description and examples of the invention the following abbreviations will be used:
BID One dose twice daily
CDR Complementarity determining region
CHO Chinese hamster ovary
DFS Disease free survival
DLT Dose limiting toxicity
FFPE formalin-fixed, paraffin-embedded
FR Framework region
HNSC Head/neck squamous cell carcinoma.
IgG Immunoglobulin G
IHC Immunohistochemistry or immunohistochemical
MDSC Myeloid derived suppressor cell
MTD Maximum tolerated dose
NCBI National Center for Biotechnology Information
NCI National Cancer Institute
OR Overall response
OS Overall survival
PD Progressive disease
PFS Progression free survival
PR Partial response
Q1W One dose every one week
Q2W One dose every two weeks
Q3W One dose every three weeks
Q4W One dose every four weeks
QD One dose per day
RECIST Response Evaluation Criteria in Solid Tumors
SD Stable disease
VH Immunoglobulin heavy chain variable region
VK Immunoglobulin kappa light chain variable region

I. Definitions

So that the invention may be more readily understood, certain technical and scientific terms are specifically defined below. Unless specifically defined elsewhere in this document, all other technical and scientific terms used herein have the meaning commonly understood by one of ordinary skill in the art to that this invention belongs.

"About" when used to modify a numerically defined parameter (e.g., the dose of an anti-CCR4 antibody or 4-1BB agonist, or the length of treatment time with a combination therapy described herein) means that the parameter may vary by as much as 10% below or above the stated numerical value for that parameter. For example, a dose of about 5 mg/kg may vary between 4.5 mg/kg and 5.5 mg/kg.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

As used herein, the term "antibody" refers to any form of immunoglobulin molecule that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic. As used herein, the term "antibody" encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "4-1BB antibody" as used herein means an antibody, as defined herein, capable of binding to human 4-1BB receptor.

"Variable regions" or "V region" or "V chain" as used herein means the segment of IgG chains that is variable in sequence between different antibodies. It extends to Kabat residue 109 in the light chain and 113 in the heavy chain. A "variable region" of an antibody refers to the variable region of the antibody light chain or the variable region of the antibody heavy chain, either alone or in combination. Typically, the variable regions of both the heavy and light chains comprise three hypervariable regions, also called complementarity determining regions (CDRs), that are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, lung adenocarcinoma, head/neck squamous cell cancer, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, rectal cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, bone cancer, Ewing's sarcoma, cervical cancer, brain cancer, stomach cancer, bladder cancer, hepatoma, breast cancer, colon carcinoma, uterine cancer, ovarian cancer, and head and neck cancer. A variety of cancers where 4-1BB or CCR4 are implicated, whether malignant or benign and whether primary or secondary, may be treated or prevented with a method provided by the disclosure. Particularly preferred cancers that may be treated in accordance with the present invention include those characterized by expression of CCR4 in tested tissue samples.

"Biotherapeutic agent" means a biological molecule, such as an antibody or fusion protein, that blocks ligand/receptor signaling in any biological pathway that supports tumor maintenance and/or growth or suppresses the anti-tumor immune response.

"CDR" or "CDRs" as used herein means complementarity determining region(s) in a immunoglobulin variable region, defined using the Kabat numbering system, unless otherwise indicated.

"Chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that inhibit expression of genes implicated in abnormal cell proliferation or tumor growth. Chemotherapeutic agents useful in the treatment methods of the present invention include cytostatic and/or cytotoxic agents.

The antibodies and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "simultaneous administration" as used herein in relation to the administration of medicaments refers to the administration of medicaments such that the individual medicaments are present within a subject at the same time. In addition to the concomitant administration of medicaments (via the same or alternative routes), simultaneous administration may include the administration of the medicaments (via the same or an alternative route) at different times.

The Bliss independence combined response C for two single compounds with effects A and B is $C=A+B-A*B$, where each effect is expressed as a fractional inhibition between 0 and 1. (Reference: Bliss (1939) *Annals of Applied Biology*) The Bliss value, defined to be the difference between the experimental response and the calculated Bliss Independence value, indicates whether the two compounds in combination are additive or synergistic.

A Bliss value of zero (0) is considered additive. The term "additive" means that the result of the combination of the two targeted agents is the sum of each agent individually.

"Chothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, an anti-CCR4 antibody that consists essentially of a recited amino acid sequence may also include one or more amino acids, including substitutions of one or more amino acid residues, which do not materially affect the properties of the binding compound.

"Anti-CCR4 antibody" means an antibody which specifically binds to CCR4.

As used herein, an anti-human CCR4 refers to an antibody that specifically binds to human CCR4. One exemplary human CCR4 molecule consists of the following sequence:

```
                                      (SEQ ID NO: 25)
MNPTDIADTT LDESIYSNYY LYESIPKPCT KEGIKAFGEL

FLPPLYSLVF VFGLLGNSVV VLVLFKYKRL RSMTDVYLLN

LAISDLLFVF SLPFWGYYAA DQWVFGLGLC KMISWMYLVG

FYSGIFFVML MSIDRYLAIV HAVFSLRART LTYGVITSLA

TWSVAVFASL PGFLFSTCYT ERNHTYCKTK YSLNSTTWKV

LSSLEINILG LVIPLGIMLF CYSMIIRTLQ HCKNEKKNKA
```

```
VKMIFAVVVL FLGFWTPYNI VLFLETLVEL EVLQDCTFER

YLDYAIQATE TLAFVHCCLN PIIYFFLGEK FRKYILQLFK

TCRGLFVLCQ YCGLLQIYSA DTPSSSYTQS TMDHDLHDAL
(UniProtKB/Swiss-Prot: P51679.1; GenBank Accession
Number NM_005508.2).
```

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3. "M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Patient" or "subject" refers to any single subject for which therapy is desired or that is participating in a clinical trial, epidemiological study or used as a control, including humans and mammalian veterinary patients such as cattle, horses, dogs, and cats.

Examples of mAbs that bind to human CCR4, and useful in the treatment method, medicaments and uses of the present invention, are described in, for example, U.S. Pat. No. 8,491,902 and US20110171210. Specific anti-human CCR4 mAbs useful as the anti-CCR4 antibody in the treatment methods, medicaments and uses of the present invention include: KW-0761, a humanized IgG1 mAb with CAS Registry number 1159266-37-1 and which comprises the heavy and light chain amino acid sequences shown in FIG. 4; and the humanized antibody huCCR4, described in US20110171210, and which comprises the heavy and light chain variable region amino acid sequences shown in FIG. 3.

In some embodiments of the treatment methods, medicaments and uses of the present invention, the anti-CCR4 antibody is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In some embodiments of the treatment method, medicaments and uses of the present invention, the anti-CCR4 antibody is a monoclonal antibody which specifically binds to human CCR4 and comprises (a) a heavy chain variable region comprising SEQ ID NO: 13 and (b) a light chain variable region comprising SEQ ID NO: 14.

In some embodiments of the treatment method, medicaments and uses of the present invention, the anti-CCR4 antibody is a monoclonal antibody which specifically binds to human CCR4 and comprises (a) a heavy chain comprising SEQ ID NO: 15 and (b) a light chain comprising SEQ ID NO: 16.

Table 2 below provides a list of the amino acid sequences of exemplary anti-CCR4 mAbs for use in the treatment method, medicaments and uses of the present invention, and the sequences are shown in FIGS. 1-4.

TABLE 2

EXEMPLARY ANTI-HUMAN CCR4 MONOCLONAL ANTIBODIES

A. Comprises light and heavy chain CDRs of KW-0761 in U.S. Pat. No. 8,491,902

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |

B. Comprises light and heavy chain CDRs of Mab1567 in US20110171210

| | |
|---|---|
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

C. Comprises the huCCR4 heavy chain variable region and the huCCR4 light chain variable region in US20110171210

| | |
|---|---|
| Heavy chain VR | SEQ ID NO: 13 |
| Light chain VR | SEQ ID NO: 14 |

D. Comprises the KW-0761 heavy chain and the KW-0761 light chain in U.S. Pat. No. 8,491,902

| | |
|---|---|
| Heavy chain | SEQ ID NO: 15 |
| Light chain | SEQ ID NO: 16 |

"Sustained response" means a sustained therapeutic effect after cessation of treatment with a therapeutic agent, or a combination therapy described herein. In some embodiments, the sustained response has a duration that is at least the same as the treatment duration, or at least about 1.5, 2.0, 2.5 or 3 times longer than the treatment duration.

The terms "synergy" or "synergistic" are used to mean that the response of the combination of the two agents is more than the sum of each agent's individual response. More specifically, in the in vitro setting one measure of synergy is known as "Bliss synergy." Bliss synergy refers to "excess over Bliss independence", as determined by the Bliss value defined above. When the Bliss value is greater than zero (0), or more preferably greater than 0.2, it is considered indicative of synergy. Of course, the use of "synergy" herein also encompasses in vitro synergy as measured by additional and/or alternate methods. References herein to a combination's in vitro biological effects, including but not limited to anti-cancer effects, being greater than, or equal to, the sum of the combination's components individually, may be correlated to Bliss values. Again, the use of "synergy" herein, including whether a combination of components demonstrates activity equal to or greater than the sum of the components individually, may be measured by additional and/or alternate methods and are known, or will be apparent, to those skilled in this art.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of an anti-CCR4 antibody and a 4-1BB agonist to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/ Median tumor volume of the control×100. In some embodiments, the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some embodiments, response to a combination of the invention is any of PR, CR, PFS, DFS, OR or OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The terms "treatment regimen", "dosing protocol" and dosing regimen are used interchangeably to refer to the dose and timing of administration of each therapeutic agent in a combination of the invention.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

4-1BB comprises a signal sequence (amino acid residues 1-17), followed by an extracellular domain (169 amino acids), a transmembrane region (27 amino acids), and an intracellular domain (42 amino acids) (Cheuk A T C et al. 2004 Cancer Gene Therapy 11: 215-226). The receptor is expressed on the cell surface in monomer and dimer forms and likely trimerizes with 4-1BB ligand to signal.

4-1BB is undetectable on the surface of naive T cells but expression increases upon activation. Upon 4-1BB activation, TRAF-1 and TRAF-2, which are pro-survival members of the TNFR-associated factor (TRAF) family, are recruited to the 4-1BB cytoplasmic tail, resulting in downstream activation of NFκB and the Mitogen Activated Protein (MAP) Kinase cascade including ERK, JNK, and p38 MAP kinases. NFκB activation leads to upregulation of Bfl-1 and Bcl-XL, pro-survival members of the Bcl-2 family. The pro-apoptotic protein Bim is downregulated in a TRAF1 and Erk dependent manner (24).

The terms "4-1BB" and "4-1BB receptor" are used interchangeably in the present application, and refer to any form of 4-1BB receptor, as well as variants, isoforms, and species homologs thereof that retain at least a part of the activity of 41BB receptor. Accordingly, a binding molecule, as defined and disclosed herein, may also bind 4-1BB from species other than human. In other cases, a binding molecule may be completely specific for the human 4-1BB and may not exhibit species or other types of cross-reactivity. Unless indicated differently, such as by specific reference to human 41BB, 41BB includes all mammalian species of native sequence 41BB, e.g., human, canine, feline, equine and bovine. One exemplary human 4-1BB is a 255 amino acid protein (Accession No. NM_001561; NP_001552). One embodiment of a complete human 4-1BB amino acid sequence is provided in SEQ ID NO: 26.

"4-1BB agonist" as used herein means, any chemical compound or biological molecule, as defined herein, which upon binding to 4-1BB, (1) stimulates or activates 4-1BB, (2) enhances, increases, promotes, induces, or prolongs an activity, function, or presence of 4-1BB, or (3) enhances, increases, promotes, or induces the expression of 4-1BB.

4-1BB agonists useful in the any of the treatment method, medicaments and uses of the present invention include a monoclonal antibody (mAb), or antigen binding fragment thereof, which specifically binds to 4-1BB. Alternative names or synonyms for 4-1BB include CD137 and TNFRSF9. In any of the treatment method, medicaments and uses of the present invention in which a human individual is being treated, the 4-1BB agonists increase a 4-1BB-mediated response. In some embodiments of the treatment method, medicaments and uses of the present invention, 4-1BB agonists markedly enhance cytotoxic T-cell responses, resulting in anti-tumor activity in several models.

The mAb may be a human antibody, a humanized antibody or a chimeric antibody, and may include a human constant region. In some embodiments the human constant region is selected from the group consisting of IgG1, IgG2, IgG3 and IgG4 constant regions, and in some embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human 4-1BB, and useful in the treatment method, medicaments and uses of the present invention, are described in U.S. Pat. No. 8,337,850 and US 2013-0078240. Specific anti-human 4-1BB mAbs useful as the 4-1BB agonist in the treatment method, medicaments and uses of the present invention include PF-05082566. PF-05082566 is a fully humanized IgG2 agonist monoclonal antibody targeting 4-1BB.

In some embodiments of the treatment method, medicaments and uses of the present invention, the 4-1BB agonist is a monoclonal antibody, or antigen binding fragment thereof, which comprises: (a) light chain CDRs SEQ ID NOs: 30, 31 and 32 and heavy chain CDRs SEQ ID NOs: 27, 28 and 29.

In some embodiments of the treatment method, medicaments and uses of the present invention, the 4-1BB agonist is a monoclonal antibody, or antigen binding fragment thereof, which specifically binds to human 4-1BB and comprises (a) a heavy chain variable region comprising SEQ ID NO: 19 or a variant thereof, and (b) a light chain variable region comprising an amino acid sequence selected from the group consisting of SEQ ID NO: 20 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In some embodiments of the treatment method, medicaments and uses of the present invention, the 4-1BB agonist is a monoclonal antibody which specifically binds to human 4-1BB and comprises (a) a heavy chain amino acid sequence as set forth in SEQ ID NO: 21 and (b) a light chain amino acid sequence as set forth in SEQ ID NO: 22, with the proviso that the C-terminal lysine residue of SEQ ID NO: 21 is optionally absent.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the anti-PD-1 antibody blocks binding of human PD-L1 to human PD-1, and preferably blocks binding of both human PD-L1 and PD-L2 to human PD-1. Exemplary human PD-1 amino acid sequences can be found in NCBI Locus No.: NP_005009. Exemplary human PD-L1 and PD-L2 amino acid sequences can be found in NCBI Locus No.: NP_054862 and NP_079515, respectively.

PD-1 antagonists useful in the any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in some embodiments, the human constant region is an IgG1 or IgG4 constant region. In some embodiments, the antigen binding fragment is selected from the group consisting of Fab, Fab'-SH, F(ab')$_2$, scFv and Fv fragments.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

II. Methods, Uses and Medicaments

Provided here are methods for treating a cancer in an individual comprising administering to the individual a combination therapy which comprises an anti-CCR4 antibody and a 4-1BB agonist. In some embodiments, the combination therapy comprises an anti-CCR4 antibody, a 4-1BB agonist and a PD-1 antagonist.

The combination therapy may also comprise one or more additional therapeutic agents. The additional therapeutic agent may be, e.g., a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, PD-1, TIM-3, LAG-3, GITR, CD137, ICOS, CD28, CD27, HVEM, BTLA, VISTA, CCR8, TIGIT, CD4, ARHGEF6, IKZF1, PTPRC, DOCK2, CCR4, CCR5, IL21R, IL2RB, NCKAP1L, SLAMF1, ITGAL, IL10RA, P2RY10, IL2RA, FMNL1, DOCK10, ITK, SASH3, KIAA0748, LCP2, TNFRSF9 (4-1BB, CD137), CYBB, and CTLA4), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholinodoxorubicin, cyanomorpholino-doxorubicin, 2-pyrrolinodoxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

Dosage units may be expressed in mg/kg (i.e. mg/kg of body weight) or mg/m$^2$. The mg/m$^2$ dosage units refer to the quantity in milligrams per square meter of body surface area.

In some instances, anti-CCR4 antibody and the 4-1BB agonist are combined or co-formulated in a single dosage form.

Although the simultaneous administration of the anti-CCR4 antibody, and the 4-1BB agonist may be maintained throughout a period of treatment or prevention, anti-cancer activity may also be achieved by subsequent administration of one compound in isolation (for example, anti-CCR4 antibody without the 4-1BB agonist, following combination treatment, or alternatively the 4-1BB agonist, without anti-CCR4 antibody, following combination treatment).

In some embodiments, the 4-1BB agonist is administered before administration of the anti-CCR4 antibody, while in other embodiments, the 4-1BB agonist is administered after administration of the anti-CCR4 antibody.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation or by imaging techniques well known in the art, such as MRI, ultrasound, or CAT scan. In some embodiments, a combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

A combination therapy of the invention is preferably administered to a human patient who has a cancer that tests positive for CCR4 expression. In some embodiments, CCR4 expression is detected using a diagnostic anti-human CCR4 antibody in an immunohistochemistry (IHC) assay on an FFPE or frozen tissue section of a tumor sample removed from the patient. Typically, the patient's physician would order a diagnostic test to determine CCR4 expression in a tumor tissue sample removed from the patient prior to initiation of treatment with the anti-CCR4 antibody and 4-1BB agonist, but it is envisioned that the physician could order the first or subsequent diagnostic tests at any time after initiation of treatment, such as for example after completion of a treatment cycle.

In one embodiment, the dosage regimen is tailored to the particular patient's conditions, response and associate treatments, in a manner which is conventional for any therapy, and may need to be adjusted in response to changes in conditions and/or in light of other clinical conditions.

In some embodiments, selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least about 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human CCR4 mAb as the anti-CCR4 antibody in the combination therapy, the dosing regimen will comprise administering the anti-human CCR4 mAb at a dose of about 0.5, 1, 2, 3, 5 or 10 mg/kg at intervals of about 7 days (+2 days) or 14 days (±2 days) or about 21 days (±2 days) or about 30 days (±2 days) throughout the course of treatment.

In some embodiments that employ an anti-human CCR4 mAb as the anti-CCR4 antibody in the combination therapy, the dosing regimen will comprise administering the anti-human CCR4 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose. In certain embodiments, the dosing interval will be about 7 days (±2 days), for doses subsequent to the second dose.

In some embodiments, a subject will be administered an intravenous (IV) infusion of a medicament comprising any of the anti-CCR4 antibodies described herein.

In some embodiments, the anti-CCR4 antibody in the combination therapy is KW-0761, which is administered intravenously at a dose selected from the group consisting of: about 0.5 mg/kg Q2W, 1 mg/kg Q2W, 2 mg/kg Q2W, 3 mg/kg Q2W, 5 mg/kg Q2W, 10 mg/kg Q2W, 1 mg/kg Q3W, 2 mg/kg Q3W, 3 mg/kg Q3W, 5 mg/kg Q3W, and 10 mg/kg Q3W. In some embodiments, anti-CCR4 antibody is administered as a liquid medicament which comprises 0.01-150 mg/mL KW-0761, 10-30 mg/mL Glycine in 0.1-50 mM citrate buffer pH 4-7, and the selected dose of the medicament is administered by IV infusion dissolved in 200-250 mL saline over a time period of about 2 hrs. In another embodiment, anti-CCR4 antibody is administered as a liquid medicament which comprises 4 mg/mL KW-0761, 22.5 mg/mL Glycine, 0.02% (w/v) polysorbate 80 in citrate buffer pH 5.2-5.8, and the selected dose of the medicament is administered by IV infusion dissolved in 200-250 mL saline over a time period of about 2 hrs.

In some embodiments, the anti-CCR4 antibody in the combination therapy is KW-0761, which is administered in a liquid medicament at a dose selected from the group consisting of 0.5 mg/kg Q1W, 0.5 mg/kg Q2W, 1 mg/kg Q1W, 1 mg/kg Q2W, 2 mg/kg Q2W, 3 mg/kg Q2W, 5 mg/kg Q2W, 10 mg/kg Q2W, 1 mg/kg Q3W, 2 mg/kg Q3W, 3 mg/kg Q3W, 5 mg/kg Q3W, and 10 mg/kg Q3W. In some embodiments, KW-0761 is administered as a liquid medicament which comprises 25 mg/ml KW-0761, 7% (w/v) sucrose, 0.02% (w/v) polysorbate 80 in 10 mM histidine buffer pH 5.5, and the selected dose of the medicament is administered by IV infusion over a time period of about 30 minutes. In another embodiment, KW-0761 is administered as a liquid medicament which comprises 0.01-150 mg/mL KW-0761, 10-30 mg/mL Glycine in 0.1-50 mM citrate buffer pH 4-7, and the selected dose of the medicament is administered by IV infusion dissolved in 200-250 mL saline over a time period of about 2 hrs. In another embodiment, KW-0761 is administered as a liquid medicament which comprises 4 mg/mL KW-0761, 22.5 mg/mL Glycine, 0.02% (w/v) polysorbate 80 in citrate buffer pH 5.2-5.8, and the selected dose of the medicament is administered by IV infusion dissolved in 200-250 mL saline over a time period of about 2 hrs.

In some embodiments, the 4-1BB agonist in the combination therapy is PF-05082566, which is administered in a liquid medicament at a dose selected from the group consisting of 0.24 mg/ml Q2W, 1.2 mg/kg Q2W, 2.4 mg/kg Q2W, 3 mg/kg Q2W, 5 mg/kg Q2W, 10 mg Q2W, 0.24 mg/ml Q3W, 1.2 mg/kg Q3W, 2.4 mg/kg Q3W, 3 mg/kg Q3W, 5 mg/kg Q3W, and 10 mg Q3W, including equivalent fixed doses. In some embodiments, PF-05082566 is administered as a liquid medicament, and the selected dose of the medicament is administered by IV infusion over a time period of about 60 minutes.

An optimal dose for KW-0761 in combination with PF-05082566 may be identified by dose escalation of one or both of these agents.

In one embodiment, KW-0761 is administered at a starting dose of 1.0 mg/kg Q2W and PF-05082566 is administered Q4W at a dose of 0.24 mg/kg, 0.3 mg/kg, 0.6 mg/kg, 1.2 mg/kg, 2.4 mg/kg, 5 mg/kg, 10 mg/kg, or at equivalent fixed doses.

In another embodiment, KW-0761 is administered at a starting dose of 0.5 mg/kg Q3W and PF-05082566 is administered Q3W at a starting dose of 0.3 mg/kg, 0.6 mg/kg, 1.2 mg/kg, 2.4 mg/kg, 5 mg/kg, or 10 mg/kg.

In yet another embodiment, PF-05082566 is administered at a starting dose of 0.3 mg/kg Q4W and KW-0761 is administered at a starting dose of 1 mg/kg Q2W, and if the starting dose combination is not tolerated by the patient, then the dose of KW-0761 is reduced to 0.5 mg/kg Q2W and/or the dose of PF-05082566 is reduced to 0.3 mg/kg Q4W.

In some embodiments, the treatment is administered in 4-week cycles. In some embodiments, PF-05082566 is administered every 4 weeks (Q4W), on day 1 of each cycle. In some embodiments, PF-05082566 is administered as a 1-hour intravenous (IV) infusion. In some embodiments, the starting dose of PF-05082566 is 1.2 mg/kg.

In some embodiments, KW-0761 is administered every week (QW), for 4 consecutive weeks (days 1, 8, 15 and 22) followed by biweekly dosing (days 1 and 15), at the dose of 1 mg/kg. In some embodiments, PF-05082566 is administered as a 1-hour IV infusion.

In some embodiments, day 1 of each dosing cycle, in which the drugs are co-administered, the KW-0761 infusion starts 30 minutes (±10 min) after completion of PF-05082566 infusion and after the post-PF-05082566 and pre-KW-0761 PK blood samples are drawn.

In some embodiments, KW-0761 is administered as a 1-hour intravenous infusion every week (ie, on Days 1, 8, 15, 22) on first cycle. In another embodiment, from cycle 2 onwards, KW-0761 is administered every 2 weeks (ie, on Days 1 and 15 of every cycle). In some embodiments, on day 1, KW-0761 infusion starts 30 minutes (±10 min) after completion of PF-05082566 infusion and after the post-PF-05082566 and pre-KW-0761 pharmacokinetic blood samples are drawn.

In some embodiments, the dosage regimen is one of the dose combinations shown in Table 3 below.

TABLE 3

| KW-0761 | and | PF-05082566 |
|---------|-----|-------------|
| 1 mg/kg | and | 0.2 mg/kg |
| 1 mg/kg | and | 0.3 mg/kg |
| 1 mg/kg | and | 0.5 mg/kg |
| 1 mg/kg | and | 1.2 mg/kg |
| 1 mg/kg | and | 2.4 mg/kg |
| 1 mg/kg | and | 5.0 mg/kg |
| 1 mg/kg | and | 10 mg/kg |
| 0.5 mg/kg | and | 0.2 mg/kg |
| 0.5 mg/kg | and | 0.3 mg/kg |
| 0.5 mg/kg | and | 0.5 mg/kg |
| 0.5 mg/kg | and | 1.2 mg/kg |
| 0.5 mg/kg | and | 2.4 mg/kg |
| 0.5 mg/kg | and | 5.0 mg/kg |
| 0.5 mg/kg | and | 10 mg/kg |
| 0.1 mg/kg | and | 0.2 mg/kg |
| 0.1 mg/kg | and | 0.3 mg/kg |
| 0.1 mg/kg | and | 0.5 mg/kg |
| 0.1 mg/kg | and | 1.2 mg/kg |
| 0.1 mg/kg | and | 2.4 mg/kg |
| 0.1 mg/kg | and | 5.0 mg/kg |
| 0.1 mg/kg | and | 10 mg/kg |

In some embodiments, treatment with study drugs continues until completion of 24 months of treatment (approximately 24 cycles), confirmed disease progression, patient refusal, unacceptable toxicity, whichever occurs first, the study may be prematurely terminated.

In the event of significant toxicity dosing may be delayed and/or reduced. In some embodiments, the dose modification may occur within a cycle. For example, dosing may be interrupted until adequate recovery and dosing may be reduced, if required, during a given treatment cycle. In another embodiment, dosing may be modified between cycles. For example, the next cycle administration may be delayed due to persisting toxicity when a new cycle is due to start. In yet another embodiment, dosing may be modified in the next cycle. For example, dose reduction may be required in a subsequent cycle based on toxicity experienced in the previous cycle. In some embodiments, treatment with PF 05082566 and/or KW-0761 can be resumed after all toxicities have recovered within the limits described herein.

In some embodiments, dosage levels below the lower limit of the aforesaid range may be more than adequate, while in other cases still larger doses may be employed, as determined by those skilled in the art.

In some embodiments, a treatment cycle begins with the first day of combination treatment and last for 3 weeks or 4 weeks. On any day of a treatment cycle that the drugs are co-administered, the KW-0761 IV infusion preferably begins 30 minutes after completion of the PF-05082566 infusion. Alternatively, KW-0761 is administered by IV infusion after completion of the PF-05082566 infusion. The invention also contemplates simultaneous IV infusion of PF-05082566 and KW-0761.

In some embodiments, the combination therapy is preferably administered for at least 12 weeks (three 4 week cycles or four 3 week cycles), more preferably at least 24 weeks, and even more preferably at least 2 to 4 weeks after the patient achieves a CR.

In another embodiment, a response to the combination therapy is assessed using RECIST version 1.1 and irRC. Tumor assessments will include all known or suspected disease sites. In one embodiment, imaging may include chest, abdomen and pelvis CT or MRI scans; brain CT or MRI scan, and bone scans (if needed). In yet another embodiment, the CT scans are performed with contrast agents unless contraindicated for medical reasons. In another embodiment, same imaging technique used to characterize each identified and reported lesion at baseline is employed in the following tumor assessments. In another embodiment, antitumor activity is assessed through radiological tumor assessments conducted at baseline, on treatment every 8 weeks up to 1 year, then every 3 months and whenever disease progression is suspected (e.g., symptomatic deterioration). In yet another embodiment, confirmation of response (CR/PR) is done at least 4 weeks after the initial response. In some embodiments, the allowable time window for disease assessments is up to −7 days for screening (i.e., the screening time window is up to 35 days prior to registration) and ±7 days, on treatment, starting from C1D1. In another embodiment, the timing follows calendar days and should not be adjusted for delays in cycle starts.

In some embodiments, the patient selected for treatment with the combination therapy of the invention has been diagnosed with an advanced solid malignant tumor. Preferably, the patient has not received prior systemic therapy for the advanced tumor.

The present invention also provides a medicament which comprises an anti-CCR4 antibody as described above and a pharmaceutically acceptable excipient. When the anti-CCR4 antibody is a biotherapeutic agent, e.g., a mAb, the antagonist may be produced in CHO cells using conventional cell culture and recovery/purification technologies.

In some embodiments, a medicament comprising an anti-CCR4 antibody as the anti-CCR4 antibody may be provided as a liquid formulation or prepared by reconstituting a lyophilized powder with sterile water for injection prior to use. In some embodiments, a medicament comprising KW-0761 is provided in a glass vial which contains about 50 mg of KW-0761.

The present invention also provides a medicament which comprises a 4-1BB agonist antibody and a pharmaceutically acceptable excipient. The 4-1BB agonist antibody may be prepared as described in U.S. Pat. No. 8,337,850.

In some embodiments, the 4-1BB agonist antibody may be formulated at a concentration of 10 mg/mL to allow intravenous (IV). The commercial formulation may contain L-histidine buffer with α,α-trehalose dihydrate, disodium ethylenediaminetetraacetic acid dihydrate and polysorbate 80 at pH 5.5.

The anti-CCR4 and 4-1BB medicaments described herein may be provided as a kit which comprises a first container and a second container and a package insert. The first container contains at least one dose of a medicament comprising an anti-CCR4 antibody, the second container contains at least one dose of a medicament comprising a 4-1BB agonist, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some embodiments of the kit, the anti-CCR4 antibody is KW-0761 and the instructions state that the medicaments are intended for use in treating a patient having a cancer that tests positive for CCR4 expression.

These and other aspects of the invention, including the exemplary specific embodiments listed below, will be apparent from the teachings contained herein.

Exemplary Specific Embodiments of the Invention

1. A method for treating a cancer in an individual comprising administering to the individual a combination therapy which comprises an anti-CCR4 antibody and a 4-1BB agonist.
2. A medicament comprising an anti-CCR4 antibody for use in combination with a 4-1BB agonist for treating a cancer in an individual.
3. A medicament comprising a 4-1BB agonist for use in combination with an anti-CCR4 antibody for treating a cancer in an individual.
4. The medicament of embodiment 3 or 4, which further comprises a pharmaceutically acceptable excipient.
5. Use of an anti-CCR4 antibody in the manufacture of medicament for treating a cancer in an individual when administered in combination with a 4-1BB agonist.
6. Use of a 4-1BB agonist compound in the manufacture of a medicament for treating a cancer in an individual when administered in combination with an anti-CCR4 antibody.
7. Use of an anti-CCR4 antibody and a 4-1BB agonist in the manufacture of medicaments for treating a cancer in an individual.
8. A kit which comprises a first container, a second container and a package insert, wherein the first container comprises at least one dose of a medicament comprising an anti-CCR4 antibody, the second container comprises at least one dose of a medicament comprising a 4-1BB agonist, and the package insert comprises instructions for treating an individual for cancer using the medicaments.
9. The kit of embodiment 8, wherein the instructions state that the medicaments are intended for use in treating an individual having a cancer that tests positive for CCR4 expression by, for example, an immunohistochemical (IHC) assay.
10. The method, medicament, use or kit of any of embodiments 1 to 9, wherein the individual is a human and the anti-CCR4 antibody is a monoclonal antibody that specifically binds to human CCR4 and depletes $CD4^+$ cells.
11. The method, medicament, use or kit of embodiment 9, wherein the anti-CCR4 antibody is KW-0761 or huCCR4.
12. The method, medicament, use or kit of any of embodiments 1 to 9, wherein the individual is a human, and the anti-CCR4 antibody is a monoclonal antibody that specifically binds to human CCR4.
13. The method, medicament, use or kit of embodiment 12, wherein the anti-CCR4 antibody depletes $CD4^+$ cells.
14. The method, medicament, use or kit of embodiment 13, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.
15. The method, medicament, use or kit of embodiment 13, wherein the monoclonal antibody, or antigen binding fragment thereof, comprises light chain CDRs of SEQ ID NOs: 7, 8 and 9 and heavy chain CDRs of SEQ ID NOs: 10, 11 and 12.
16. The method, medicament, use or kit of embodiment 13, wherein the anti-CCR4 antibody comprises a heavy chain and a light chain, and wherein the heavy chain comprises SEQ ID NO: 15 and the light chain comprises SEQ ID NO: 16.
17. The method, medicament, use or kit of embodiment 13, wherein the anti-CCR4 antibody comprises heavy and light chain variable regions, and wherein the heavy chain variable region comprises SEQ ID NO: 17 and the light chain variable region comprises SEQ ID NO: 18.

18. The method, medicament, use or kit of any of embodiments 10-17, wherein the cancer is a solid tumor.

19. The method, medicament, use or kit of any of embodiments 10-17, wherein the cancer is bladder cancer, breast cancer, clear cell kidney cancer, head/neck squamous cell carcinoma, rectal carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer.

20. The method, medicament, use or kit of any of embodiments 10-17, wherein the individual has not been previously treated for an advanced solid malignant tumor.

21. The method, medicament, use or kit of any of embodiments 10-17, wherein the cancer is acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

22. The method, medicament, use or kit of any of embodiments 10-21, wherein the 4-1BB agonist is a monoclonal antibody which comprises the heavy chain and light chain variable regions of SEQ ID NO: 19 and SEQ ID NO: 20, respectively.

23. The method, medicament, use or kit of embodiments 10-21, wherein the 4-1BB agonist is a monoclonal antibody which comprises light chain CDRs of SEQ ID NOs: 30, 31 and 32 and heavy chain CDRs of SEQ ID NOs: 27, 28 and 29.

24. The method, medicament, use or kit of embodiments 10-21, wherein the 4-1BB agonist is a monoclonal antibody which comprises a heavy chain and a light chain, and wherein the heavy chain comprises SEQ ID NO: 21 and the light chain comprises SEQ ID NO: 22.

25. The method, medicament, use or kit of any of embodiments 10-22, the cancer tests positive for human CCR4.

26. The method, medicament, use or kit of embodiment 23, wherein the human CCR4 expression is elevated.

27. The method, medicament, use or kit of embodiment 14, wherein the anti-CCR4 antibody is KW-0761 or huCCR4.

28. The method, medicament, use or kit of embodiment 25, wherein the KW-0761 is formulated as a liquid medicament which comprises 4 mg/mL anti-CCR4 antibody, 22.5 mg/mL Glycine, 0.02% (w/v) polysorbate 80 in citrate buffer pH 5.2-5.8.

29. The method, medicament, use or kit of any of embodiments 1 to 26, wherein the 4-1BB agonist is PF-05082566.

30. The method, medicament, use or kit of any of embodiments 1 to 26,
wherein the anti-CCR4 antibody is administered at a dose of about 0.5, 1, 2, 3, 5 or 10 mg/kg.

31. The method, medicament, use of kit of any of embodiments 1 to 26, wherein the anti-CCR4 antibody is KW-0761, the 4-1BB agonist is PF-05082566, the individual is diagnosed with an advanced malignant solid tumor, and doses of the anti-CCR4 antibody and 4-1BB agonist are selected from the group consisting of one of the combinations in the table below:

TABLE 4

| KW-0761 | and | PF-05082566 |
|---|---|---|
| 1 mg/kg | and | 0.2 mg/kg |
| 1 mg/kg | and | 0.3 mg/kg |
| 1 mg/kg | and | 0.5 mg/kg |
| 1 mg/kg | and | 1.2 mg/kg |
| 1 mg/kg | and | 2.4 mg/kg |
| 1 mg/kg | and | 5.0 mg/kg |
| 1 mg/kg | and | 10 mg/kg |
| 0.5 mg/kg | and | 0.2 mg/kg |
| 0.5 mg/kg | and | 0.3 mg/kg |
| 0.5 mg/kg | and | 0.5 mg/kg |
| 0.5 mg/kg | and | 1.2 mg/kg |
| 0.5 mg/kg | and | 2.4 mg/kg |
| 0.5 mg/kg | and | 5.0 mg/kg |
| 0.5 mg/kg | and | 10 mg/kg |
| 0.1 mg/kg | and | 0.2 mg/kg |
| 0.1 mg/kg | and | 0.3 mg/kg |
| 0.1 mg/kg | and | 0.5 mg/kg |
| 0.1 mg/kg | and | 1.2 mg/kg |
| 0.1 mg/kg | and | 2.4 mg/kg |
| 0.1 mg/kg | and | 5.0 mg/kg |
| 0.1 mg/kg | and | 10 mg/kg |

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol. 1*, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol. 2*, John Wiley and Sons, Inc., New York; Ausubel, et al. (2001) *Current Protocols in Molecular Biology, Vol. 3*, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1. Combination Treatment

This example illustrates the effect of $CD4^+$ T cell depletion on the anti-tumor activity of 4-1BB agonist antibody in animal cancer models.

To evaluate the anti-tumor efficacy of combination immunotherapy against established B16F10 tumors, an anti-4-1BB dosing regimen was selected based on prior studies that showed efficacy in the CT26 model (Escuin-Ordinas et al., J Immunother Cancer, 2013; 1:14) and anti-PD-1 and anti-LAG-3 dosing regimens as previously reported (Woo et al., Cancer Research, 2012; 72:917-27; Curran et al., PloS One. 2011; 6:e19499). Consistent with published results, anti-4-1BB, anti-PD-1 or anti-LAG-3 alone did not consistently inhibit B16F10 tumor growth when these single agent treatments were started in tumors of 50-154 $mm^3$ in size (data not shown). Combining anti-PD-1 with anti-LAG-3 resulted in 54% of tumor growth inhibition (TGI) relative to the isotype control (p<0.001), although no mice were tumor free after this treatment. By contrast, when animals were concurrently administrated anti-4-1BB and anti-PD-1 antibodies, a dramatic efficacy of 85% TGI relative to isotype controls (p<0.0001) ensued and 7 of 10 treated animals were tumor free (data not shown). Such remarkable combinatorial efficacy is reproducible: in an independent study (tumor size between 64-209 $mm^3$) by different experimentalists, the average tumor burden was reduced in the combination treatment group, with 2/10 animals completely tumor free and 4/10 animals having ongoing, partial regression at the end of the study (data not shown). Furthermore, significant TGI (51% relative to the control group, p<0.0001) was only observed for the anti-4-1BB/anti-PD-1 combination when treatment was applied to very large tumors (size between 126-350 $mm^3$), whereas the anti-PD-1/anti-LAG-3 combination was ineffective (data not shown).

Likewise, a robust anti-tumor effect of the anti-4-1BB/anti-PD-1 combination was observed in the MC38 colon cancer model (data not shown). At the end of the study (day 21 post tumor implant), the TGI for the combination treatment was 63% relative to the PBS control. The suppression was also significant when compared to single agent alone treatments (p<0.05 vs. anti-4-1BB alone and p<0.001 vs. anti-PD-1 alone).

To determine the immune cell subsets that are required for the anti-4-1BB/anti-PD-1 combination treatment, antibodies were used to deplete either $CD4^+$ T cells, $CD8^+$ T cells, or both $CD4^+$ and $CD8^+$ T cells simultaneously in B16F10-bearing mice. On day 0, C57BL/6 mice were inoculated s.c. with $1 \times 10^6$ B16F10. Mice were randomized into groups of 10 animals per group with an average tumor volume of ~80 $mm^3$ (day 10). B16F10-bearing mice received anti-CD4 (GK1.5, BioXcell) and/or anti-CD8 (53.5.8, BioXcell) as described previously (Butler et al., Nature Immunology, 2012; 13:188-95). Briefly, one hundred (100) µg of isotype control IgG or anti-CD4 and/or anti-CD8 mAbs was administered i.p. on days 11, 16, and 21. Anti-4-1BB (1 mg/kg)/anti-PD-1 (10 mg/kg) mAbs were dosed on days 12, 17 and 22. Tumor size was measured 2-3 times a week.

Tumor growth after anti-4-1BB agonist antibody+anti-PD-1 antagonist antibody combination treatment was compared (FIG. 9). Mean±SEM of each treatment group is shown in FIG. 9. In the absence of $CD8^+$ T cells, the tumor suppression was completely abrogated. Interestingly, depletion of $CD4^+$ T cells resulted in an enhanced anti-tumor activity (p<0.05 vs. anti-4-1BB/anti-PD-1 group). These data indicate that Treg cell depletion enhances the anti-tumor activity of 4-1BB agonist.

Figure 10:
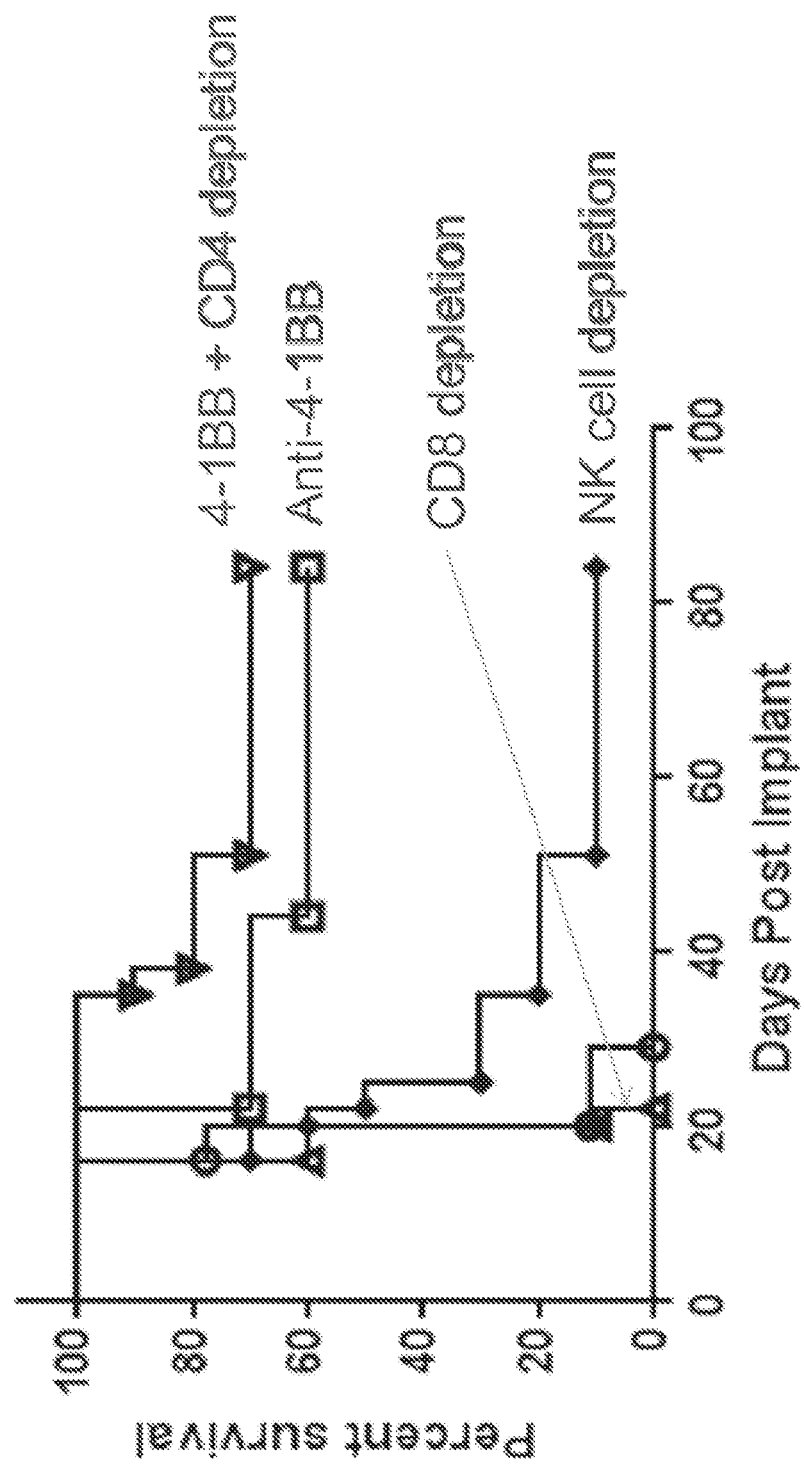
FIG. 10 depicts a graph showing the effect of CD4+ T cell depletion on 4-1BB agonist antibody treatment, PD-1 antagonist antibody treatment, and combination treatment in a CT26 colon tumor model.

In a separate experiment, the effect of CD4+ T cell depletion on anti-4-1BB/anti-PD-1 combination treatment in the CT26 colon tumor model was evaluated (FIG. 10). In the absence of CD8+ T cells, the tumor suppression was completely abrogated. As in the B16 melanoma model, depletion of CD4+ T cells resulted in an enhanced anti-tumor activity.

These results demonstrate that anti-tumor activity of 4-1BB agonist antibody can be augmented by depletion of Treg cells or CD4+ T cells in tumor models.

Materials and Methods

Mice.

Six- to 8-week old female C57BL/6 mice were purchased from The Jackson Laboratories. Mice were maintained and all animal experiments were conducted according to the protocols approved by the Institutional Animal Care and Use Committee of Rinat, South San Francisco and Worldwide Research and Development (WRD), La Jolla, Pfizer Inc.

Cell Lines.

The B16F10 melanoma cell line was purchased from American Type Culture Collection (ATCC). MC38 colon carcinoma cell line was kindly provided by Dr. Antoni Ribas at UCLA, Los Angeles, Calif. Cells were cultured in DMEM medium supplemented with 10% fetal bovine serum, 2 mM L-glutamine at 37° C. in an atmosphere of 5% $CO_2$ in air, and IMPACT-tested for pathogens at Research Animal Diagnostic Laboratory (RADIL) (Columbia, Mo.). Pathogen-free cells growing in an exponential growth phase were harvested and used for tumor inoculation.

Antibodies for Immunotherapy and Flow Cytometry.

Therapeutic rat anti-mouse 4-1BB mAb (clone MAB9371) was purchased from R&D systems. Rat anti-mouse PD-1 mAb (clone RMP1-14) and rat IgG2a isotype control were purchased from BioXcell. Rat anti-mouse LAG-3 mAb (clone eBioC9B7W) was purchased from eBioscience.

Monoclonal antibodies used for cell surface or intracellular stains were purchased from BD Biosciences or eBioscience. Monoclonal antibodies used to characterize T cells were hamster anti-mouse CD3ε-Alexa Fluor 488 (clone 145-2C11), rat anti-mouse CD4-PerCP-Cy5.5 (Clone RM4-5), rat anti-mouse CD8α-APC-H7 (clone 53-6.7), rat anti-mouse CD25-BD Horizon V450 (clone PC61), hamster anti-mouse CD137 (4-1BB)-APC (clone 17B5), hamster anti-mouse CD279 (PD-1)-BD Horizon PE-CF594 (clone J43), rat anti-mouse FoxP3-Alexa Fluor 700 (clone FJK-16s), rat anti-mouse Eomes-PE (Clone: Dan11mag), hamster anti-mouse KLRG1-PerCP-Cy5.5 (clone 2F1), and rat anti-mouse NK-1.1-PE-Cy7 (Clone PK136). For MDSC characterization, mAbs were rat anti-mouse CD45-APC-Cy7 (clone 30-F11), rat anti-mouse CD11b-Alexa Fluor 488 (clone M1/70), rat anti-mouse Ly-6G (Gr-1)-PerCP-Cyanine5.5 (clone RB6-8C5), and rat anti-mouse F4/80-PE (clone BM8). Live cells were separated from dead cells using LIVE/DEAD Fixable Blue Dead Cell Stain Kit (Invitrogen).

Immune Cell Phenotyping Using Flow Cytometry.

Spleens from tumor-bearing mice were harvested and dissociated mechanically to single cell suspension in ice-cold PBS. Splenocytes were treated with Red Blood Cell Lysing Buffer Hybri-Max (Sigma-Aldrich) to remove red blood cells, washed twice with PBS, and resuspended in PBS supplemented with 2% FBS and 0.9% $NaN_3$. An aliquot of ~1×10$^6$ splenocytes was pre-incubated with 10 μg/mL of mouse BD Fc Block (BD Biosciences) for 10 minutes before phenotyping mAb cocktail was added to specifically stain immune cells.

Tumor infiltrating lymphocytes were prepared using mouse tumor dissociation kit and the GentleMACS Dissociator according to manufacturer's instructions (Miltenyi Biotec).

Cell surface antigens were labeled by incubating cells at 4° C. for 30 minutes. Intracellular staining was carried out using FoxP3/Transcription Factor Staining Buffer set according to the manufacturer's protocol (eBioscience). Flow cytometry data were acquired using LSR Fortessa (BD Biosciences) and analyzed using FlowJo (TreeStar Inc.).

In Vivo Tumor Efficacy Studies.

C57BL/6 mice were inoculated subcutaneously at the right flank with 1×10$^6$ B16F10 or MC38 cells in 0.1 ml of serum-free DMEM medium or PBS. Treatment was started when tumors reached 50-154 mm$^3$ in size. Antibodies to 4-1BB (1 mg/kg), PD-1 (10 mg/kg) and LAG-3 (10 mg/kg), alone or in combination, were administrated twice intraperitoneally (i.p.) 5 days apart. In the study of treating larger tumors (range of 126-350 mm$^3$), antibodies were given four times i.p. 3 days apart. Tumor size was measured in two dimensions using calipers, and the volume was expressed in mm$^3$ using the formula: $V=0.5\ L\times W^2$ where L and W are the long and short diameters of the tumor, respectively.

Example 2. Gene Expression Profiling: Analysis of Human Genes Correlating with FOXP3 mRNA in Human Tumors This Example illustrates the correlation of CCR4 mRNA with FOXP3 mRNA in human tumors.

RNA-Seq data from The Cancer Genome Atlas (TCGA) was analyzed to identify the correlation between human genes and FOXP3 mRNA in human tumors. Table 5 below provides a list of human genes by the order of their mean correlation coefficient with FOXP3 mRNA (tumor RNAseq data) across three tumor types. Higher correlation coefficient value indicates potentially higher efficacy in depleting Tregs. Genes in bold are well-known genes associated with activated Treg cells.

Based on correlation analysis with FOXP3 across multiple solid tumor RNA-Seq data from TCGA, CCR4 was identified as an attractive target for depleting Treg cells. CCR4 has relatively high FOXP3 correlation coefficient values of 0.857, 0.837, and 0.856 in HNSC tumor, colon tumor and rectal tumor, respectively (Table 5). Other targets for depleting Treg cells identified in this study include: CCR8, ICOS, TIGIT, CD4, CD28, ARHGEF6, IKZF1, PTPRC, DOCK2, CCR4, CCR5, IL21R, IL2RB, NCKAP1L, SLAMF1, ITGAL, IL10RA, P2RY10, IL2RA, FMNL1, DOCK10, ITK, SASH3, KIAA0748, LCP2, TNFRSF9 (4-1BB, CD137), CYBB and CTLA4.

TABLE 5

| | Correlation Coefficient with FOXP3 mRNA | | | |
|---|---|---|---|---|
| Gene | HNSC Tumor | Colon Tumor | Rectal Tumor | Mean |
| CCR8 | 0.914 | 0.910 | 0.885 | 0.903 |
| ICOS | 0.870 | 0.847 | 0.874 | 0.864 |
| TIGIT | 0.878 | 0.833 | 0.876 | 0.862 |
| CD4 | 0.864 | 0.862 | 0.851 | 0.859 |
| CD28 | 0.900 | 0.835 | 0.838 | 0.858 |
| ARHGEF6 | 0.839 | 0.844 | 0.880 | 0.854 |
| IKZF1 | 0.895 | 0.821 | 0.841 | 0.852 |
| PTPRC | 0.885 | 0.823 | 0.846 | 0.851 |
| DOCK2 | 0.886 | 0.826 | 0.841 | 0.851 |
| CCR4 | 0.857 | 0.837 | 0.856 | 0.850 |
| CCR5 | 0.856 | 0.833 | 0.856 | 0.848 |
| IL21R | 0.884 | 0.826 | 0.830 | 0.847 |
| IL2RB | 0.884 | 0.834 | 0.820 | 0.846 |
| NCKAP1L | 0.880 | 0.818 | 0.825 | 0.841 |
| SLAMF1 | 0.856 | 0.833 | 0.824 | 0.838 |
| ITGAL | 0.853 | 0.822 | 0.827 | 0.834 |
| IL10RA | 0.858 | 0.827 | 0.815 | 0.834 |
| P2RY10 | 0.883 | 0.801 | 0.815 | 0.833 |
| IL2RA | 0.839 | 0.822 | 0.839 | 0.833 |

TABLE 5-continued

| | Correlation Coefficient with FOXP3 mRNA | | | |
|---|---|---|---|---|
| Gene | HNSC Tumor | Colon Tumor | Rectal Tumor | Mean |
| FMNL1 | 0.826 | 0.818 | 0.844 | 0.829 |
| DOCK10 | 0.802 | 0.844 | 0.841 | 0.829 |
| ITK | 0.876 | 0.803 | 0.808 | 0.829 |
| SASH3 | 0.854 | 0.817 | 0.816 | 0.829 |
| KIAA0748 | 0.876 | 0.821 | 0.788 | 0.828 |
| LCP2 | 0.845 | 0.808 | 0.825 | 0.826 | mRNA and FOXP3 mRNA, and CTLA4 mRNA and FOXP3 mRNA in human tumors. Table 6 below provides the correlation coefficients across all the tumor types available in TCGA.

Based on this analysis, cancer types indicated for treatment with anti-CCR4 antibody and 4-1BB agonist include: head/neck squamous cell cancer, rectal cancer, colon cancer, squamous cell lung cancer, thyroid cancer, bladder cancer, melanoma, cervical cancer, prostate cancer, breast cancer, uterine/endometrial cancer, pancreatic cancer, lung adenocarcinoma, ovarian cancer, and papillary kidney cancer.

TABLE 6

| Tumor | FOXP3-CCR4 Correlation | FOXP3-CTLA4 Correlation | #Tumor Samples | Steiger's test statistic | Steiger's test p-val | Steiger's test adjusted p-val |
|---|---|---|---|---|---|---|
| Head&Neck | 0.857[a] | 0.782 | 425 | 4.085 | 5.27E−05 | 0.0002 |
| Rectum | 0.856[a] | 0.692 | 85 | 3.480 | 0.0008 | 0.0027 |
| Colon | 0.837[c] | 0.785[c] | 248 | 2.191 | 0.0294 | 0.0587 |
| Lung Squamous | 0.820[c] | 0.842[c] | 482 | −1.443 | 0.1496 | 0.2288 |
| Thyroid | 0.820 | 0.859[b] | 496 | −2.909 | 0.0038 | 0.0090 |
| Bladder | 0.812[c] | 0.847[c] | 211 | −1.393 | 0.1651 | 0.2385 |
| Melanoma | 0.756[a] | 0.511 | 356 | 6.813 | 4.12E−11 | 3.57E−10 |
| Cervical | 0.731[c] | 0.616[c] | 159 | 2.089 | 0.0383 | 0.06639 |
| Prostate | 0.730[a] | 0.409 | 256 | 7.437 | 1.58E−12 | 2.06E−11 |
| Breast | 0.712 | 0.852[b] | 994 | −10.540 | 1.08E−24 | 2.80E−23 |
| Uterine Endometrial | 0.699 | 0.597 | 145 | 1.795 | 0.07469 | 0.12137 |
| Pancreatic | 0.698[c] | 0.757[c] | 56 | −1.048 | 2.99E−01 | 0.38930 |
| Lung Adeno | 0.692 | 0.764[b] | 490 | −3.254 | 0.001215 | 0.00351 |
| Ovarian | 0.646 | 0.800[b] | 265 | −5.412 | 1.40E−07 | 7.29E−07 |
| Kidney Papillary | 0.600 | 0.542 | 161 | 0.997 | 0.32009 | 0.39630 |
| AML | 0.582 | 0.613 | 172 | −0.684 | 0.49489 | 0.55945 |
| Kidney Clear | 0.574 | 0.730[b] | 507 | −5.868 | 7.98E−09 | 5.19E−08 |
| B-cell lymphoma | 0.569 | 0.571 | 28 | −0.013 | 0.98997 | 0.98997 |
| Liver | 0.557 | 0.358 | 147 | 2.885 | 4.51E−03 | 0.00976 |
| Glioma | 0.520 | 0.551 | 166 | −0.527 | 5.99E−01 | 0.64900 |
| Uterine Sarcoma | 0.496 | 0.490 | 56 | 0.046 | 0.96385 | 0.98997 |
| Kidney Chromo | 0.429 | 0.609 | 66 | −2.143 | 3.59E−02 | 0.06639 |
| Sarcoma | 0.424 | 0.666 | 105 | −3.445 | 0.00083 | 0.00269 |
| Low-grade Glioma | 0.199 | 0.148 | 306 | 0.805 | 0.42152 | 0.49816 |
| Adrenal gland | 0.126 | 0.270 | 79 | −1.320 | 1.91E−01 | 0.26117 |

[a]Cancer types where CCR4 is better correlated to FOXP3
[b]Cancer types where CTLA4 is better correlated to FOXP3
[c]Cancer types where the correlation of FOXP3 to CTLA4 and CCR4 is good TABLE 5-continued

| | Correlation Coefficient with FOXP3 mRNA | | | |
|---|---|---|---|---|
| Gene | HNSC Tumor | Colon Tumor | Rectal Tumor | Mean |
| TNFRSF9 (4-1BB, CD137) | 0.822 | 0.794 | 0.857 | 0.824 |
| CYBB | 0.812 | 0.801 | 0.851 | 0.821 |
| CTLA4 | 0.782 | 0.785 | 0.692 | 0.753 |

Example 3. Gene Expression Profiling: Identification of Cancer Types Suitable for Treatment of Anti-CCR4 Antibody This Example illustrates the correlation of human gene mRNA and FOXP3 mRNA in human tumors.

RNA-Seq data from The Cancer Genome Atlas (TCGA) was analyzed to identify the correlation between CCR4

Example 4. Concurrent Administration of an Anti-CCR4 Antibody and a 4-1BB Agonist to Tumor-Bearing Mice This example illustrates anti-CCR4 antibody treatment in combination with a 4-1BB agonist in animal cancer models.

In one study, C57BL6 mice are subcutaneously implanted with $1\times10^6$ MC38 murine colon carcinoma cells. Tumor growth is monitored and animals randomized to four groups of 8 when the tumors reach an average size of 150 mm$^3$ and are intraperitoneally dosed with isotype controls, 1 mg/kg of a rat anti-mouse 4-1BB agonist monoclonal antibody (R&D Systems #MAB9371), 10 mg/kg of an anti-mouse CCR4 antibody, or the simultaneous combination of the two once every 5 days for a total of two doses. Tumor size is measured in two dimensions using calipers, and the volume was expressed in mm$^3$ using the formula: $V=0.5\ L\times W^2$ where L and W are the long and short diameters of the tumor, respectively. The study is terminated when tumor sizes of the controls reach 1000 mm³. Efficacy of the combination treatment is evaluated by comparing animals treated with 4-1BB agonist monoclonal antibody, anti-mouse CCR4 antibody, or the simultaneous combination of the two.

Example 5. Prioritizing Indications: Pursuing Patient Selection Strategies

This example illustrates strategies for patient selection for anti-CCR4 antibody/4-1BB agonist combination treatment.

Anti-CCR4 therapy depletes Tregs which suppress anti-tumor response. 4-1BB amplifies anti-tumor T cell activity. Based on the effect demonstrated by Example 1 above, anti-CCR4 antibody in combination with a 4-1BB agonist will result in an enhanced response greater than either single agent.

Tumors with high Treg (FOXP3+) content are prioritized for these studies. Patients are selected by assessing tumor-infiltrating lymphocytes (TIL) in paired pre- and post-dose fresh biopsies. Immunohistochemistry analysis is conducted to determine tumor infiltrating T cell location and activation status. 4-1BB/CCR4 ratio is assessed at baseline and after treatment. CD4, CD8, FoxP3, PD-1 and PD-L1 are evaluated in parallel.

Table 7 provides a brief description of the sequences in the sequence listing.

TABLE 7

| SEQ ID NO: | Description |
|---|---|
| 1 | KW-0761 light chain CDR1 |
| 2 | KW-0761 light chain CDR2 |
| 3 | KW-0761 light chain CDR3 |
| 4 | KW-0761 heavy chain CDR1 |
| 5 | KW-0761 heavy chain CDR2 |
| 6 | KW-0761 heavy chain CDR3 |
| 7 | Mab1567 light chain CDR1 |
| 8 | Mab1567 light chain CDR2 |
| 9 | Mab1567 light chain CDR3 |
| 10 | Mab1567 heavy chain CDR1 |
| 11 | Mab1567 heavy chain CDR2 |
| 12 | Mab1567 heavy chain CDR3 |
| 13 | huCCR4 heavy chain variable region |
| 14 | huCCR4 light chain variable region |
| 15 | KW-0761 full length heavy chain |
| 16 | KW-0761 full length light chain |
| 17 | KW-0761 heavy chain variable region |
| 18 | KW-0761 light chain variable region |
| 19 | 4-1BB agonist heavy chain variable region |
| 20 | 4-1BB agonist light chain variable region |
| 21 | 4-1BB agonist heavy chain |
| 22 | 4-1BB agonist light chain |
| 23 | Nivolumab Heavy chain |
| 24 | Nivolumab light chain |
| 25 | Human CCR4 |
| 26 | Human 4-1BB |
| 27 | 4-1BB agonist heavy chain CDR1 |
| 28 | 4-1BB agonist heavy chain CDR2 |
| 29 | 4-1BB agonist heavy chain CDR3 |
| 30 | 4-1BB agonist light chain CDR1 |
| 31 | 4-1BB agonist light chain CDR2 |
| 32 | 4-1BB agonist light chain CDR3 |

Example 6. Combination Treatment

This example illustrates combination treatment with anti-CCR4 antibody/4-1BB agonist.

PF-05082566 will be administered as a 1-hour intravenous (IV) infusion, every 4 weeks (Q4W), on Day 1 of each cycle. The starting dose of PF-05082566 will be 1.2 mg/kg.

KW-0761 will be given as a 1-hour IV infusion, every week (QW), for 4 consecutive weeks (Days 1, 8, 15 and 22) followed by biweekly dosing (Days 1 and 15), at the dose of 1 mg/kg.

On Day 1 of each dosing cycle, in which the drugs are co-administered, the KW-0761 infusion will start 30 minutes (±10 min) after completion of PF-05082566 infusion and after the post-PF-05082566 and pre-KW-0761 PK blood samples are drawn.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A method for treating cancer in an individual comprising administering to the individual an anti-CC chemokine receptor 4 (CCR4) antibody and a 4-1BB agonist, wherein the anti-CCR4 antibody comprises a heavy chain CDR1 comprising SEQ ID NO: 4, a heavy chain CDR2 comprising SEQ ID NO: 5, a heavy chain CDR3 comprising SEQ ID NO: 6; and a light chain CDR1 comprising SEQ ID NO: 1, a light chain CDR2 comprising SEQ ID NO: 2, a light chain CDR3 comprising SEQ ID NO: 3.

2. The method of claim 1, wherein the anti-CCR4 antibody comprises a heavy chain and a light chain, wherein the heavy and light chains comprise SEQ ID NO: 15 and SEQ ID NO: 16, respectively; and wherein the 4-1BB agonist is a 4-1BB agonist monoclonal antibody which comprises a heavy chain and a light chain, wherein the heavy and light chains comprise SEQ ID NO: 21 and SEQ ID NO: 22, respectively.

3. The method of claim 1, wherein the anti-CCR4 antibody comprises a heavy chain variable region comprising SEQ ID NO: 17; and a light chain variable region comprising SEQ ID NO: 18.

4. The method of claim 1, wherein the anti-CCR4 antibody and the 4-1BB agonist are administered simultaneously and sequentially.

5. The method claim 1, wherein the anti-CCR4 antibody is administered at a separate time from the 4-1 BB agonist.

6. The method of claim 1, wherein the cancer is a solid tumor.

7. The method of claim 1, wherein the cancer is head/neck squamous cell cancer, rectal cancer, colon cancer, squamous cell lung cancer, thyroid cancer, bladder cancer, melanoma, cervical cancer, prostate cancer, breast cancer, uterine/endometrial cancer, pancreatic cancer, lung adenocarcinoma, ovarian cancer, or papillary kidney cancer.

8. The method of claim 1, wherein the anti-CCR4 antibody is administered at a dose of at least about 0.5 mg/kg, about 1 mg/kg, about 2 mg/kg, about 3 mg/kg, about 5 mg/kg, or about 10 mg/kg.

9. A method for treating cancer in an individual comprising administering to the individual an anti-CC chemokine receptor 4 (CCR4) antibody and a 4-1BB agonist, wherein the 4-1BB agonist comprises a heavy chain CDR1 comprising SEQ ID NO: 27, a heavy chain CDR2 comprising SEQ ID NO: 28, a heavy chain CDR3 comprising SEQ ID NO: 29; and a light chain CDR1 comprising SEQ ID NO: 30, a light chain CDR2 comprising SEQ ID NO: 31, a light chain CDR3 comprising SEQ ID NO: 32.

10. The method of claim 9, wherein the 4-1BB agonist comprises a heavy chain variable region comprising SEQ ID NO: 19; and a light chain variable region comprising SEQ ID NO: 20.

11. The method of claim 9, wherein the anti-CCR4 antibody comprises a heavy chain and a light chain, wherein the heavy and light chains comprise SEQ ID NO: 15 and SEQ ID NO: 16, respectively; and wherein the 4-1BB agonist is a 4-1BB agonist monoclonal antibody which comprises a heavy chain and a light chain, wherein the heavy and light chains comprise SEQ ID NO: 21 and SEQ ID NO: 22, respectively.

12. The method of claim 9, wherein the anti-CCR4 antibody and the 4-1BB agonist are administered simultaneously and sequentially.

13. The method of claim 9, wherein the anti-CCR4 antibody is administered at a separate time from the 4-1BB agonist.

14. The method of claim 9, wherein the cancer is a solid tumor.

15. The method of claim 9, wherein the cancer is head/neck squamous cell cancer, rectal cancer, colon cancer, squamous cell lung cancer, thyroid cancer, bladder cancer, melanoma, cervical cancer, prostate cancer, breast cancer, uterine/endometrial cancer, pancreatic cancer, lung adenocarcinoma, ovarian cancer, or papillary kidney cancer.

16. A medicament comprising a combination of an anti-CC chemokine receptor 4 (CCR4) antibody and a 4-1BB agonist,
wherein the anti-CCR4 antibody comprises a heavy chain CDR1 comprising SEQ ID NO: 4, a heavy chain CDR2 comprising SEQ ID NO: 5, a heavy chain CDR3 comprising SEQ ID NO: 6; and a light chain CDR1 comprising SEQ ID NO: 1, a light chain CDR2 comprising SEQ ID NO: 2, a light chain CDR3 comprising SEQ ID NO: 3, or
wherein the 4-1BB agonist comprises a heavy chain CDR1 comprising SEQ ID NO: 27, a heavy chain CDR2 comprising SEQ ID NO: 28, a heavy chain CDR3 comprising SEQ ID NO: 29; and a light chain CDR1 comprising SEQ ID NO: 30, a light chain CDR2 comprising SEQ ID NO: 31, a light chain CDR3 comprising SEQ ID NO: 32.

17. The medicament of claim 16, wherein both or either of the anti-CCR4 antibody and the 4-1BB agonist are in the form of a pharmaceutical formulation to be administered simultaneously, sequentially, or concurrently.

18. The medicament of claim 16, wherein the anti-CCR4 antibody comprises a heavy chain CDR1 comprising SEQ ID NO: 4, a heavy chain CDR2 comprising SEQ ID NO: 5, a heavy chain CDR3 comprising SEQ ID NO: 6; and a light chain CDR1 comprising SEQ ID NO: 1, a light chain CDR2 comprising SEQ ID NO: 2, a light chain CDR3 comprising SEQ ID NO: 3, and wherein the 4-1BB agonist comprises a heavy chain CDR1 comprising SEQ ID NO: 27, a heavy chain CDR2 comprising SEQ ID NO: 28, a heavy chain CDR3 comprising SEQ ID NO: 29; and a light chain CDR1 comprising SEQ ID NO: 30, a light chain CDR2 comprising SEQ ID NO: 31, a light chain CDR3 comprising SEQ ID NO: 32.

19. A kit comprising a first container, a second container and a package insert, wherein the first container comprises at least one dose of a medicament comprising an anti-CC chemokine receptor 4 (CCR4) antibody, the second container comprises at least one dose of a medicament comprising a 4-1BB agonist, and the package insert comprises instructions for treating an individual for cancer using the medicaments; and
wherein the anti-CCR4 antibody comprises a heavy chain CDR1 comprising SEQ ID NO: 4, a heavy chain CDR2 comprising SEQ ID NO: 5, a heavy chain CDR3 comprising SEQ ID NO: 6; and a light chain CDR1 comprising SEQ ID NO: 1, a light chain CDR2 comprising SEQ ID NO: 2, a light chain CDR3 comprising SEQ ID NO: 3, or
wherein the 4-1BB agonist comprises a heavy chain CDR1 comprising SEQ ID NO: 27, a heavy chain CDR2 comprising SEQ ID NO: 28, a heavy chain CDR3 comprising SEQ ID NO: 29; and a light chain CDR1 comprising SEQ ID NO: 30, a light chain CDR2 comprising SEQ ID NO: 31, a light chain CDR3 comprising SEQ ID NO: 32.

20. The kit of claim 19, wherein the anti-CCR4 antibody comprises a heavy chain CDR1 comprising SEQ ID NO: 4, a heavy chain CDR2 comprising SEQ ID NO: 5, a heavy chain CDR3 comprising SEQ ID NO: 6; and a light chain CDR1 comprising SEQ ID NO: 1, a light chain CDR2 comprising SEQ ID NO: 2, a light chain CDR3 comprising SEQ ID NO: 3, and wherein the 4-1BB agonist comprises a heavy chain CDR1 comprising SEQ ID NO: 27, a heavy chain CDR2 comprising SEQ ID NO: 28, a heavy chain CDR3 comprising SEQ ID NO: 29; and a light chain CDR1 comprising SEQ ID NO: 30, a light chain CDR2 comprising SEQ ID NO: 31, a light chain CDR3 comprising SEQ ID NO: 32.

21. The kit of claim 19, wherein the instructions state that the medicaments are intended for use in treating an individual having a cancer that tests positive for CCR4 expression.

22. The kit of claim 19, wherein the cancer is head/neck squamous cell cancer, rectal cancer, colon cancer, squamous cell lung cancer, thyroid cancer, bladder cancer, melanoma, cervical cancer, prostate cancer, breast cancer, uterine/endometrial cancer, pancreatic cancer, lung adenocarcinoma, ovarian cancer, or papillary kidney cancer.

23. The kit of claim 19, wherein the cancer is a solid tumor that tests positive for CCR4 expression and is selected from the group consisting of: head/neck squamous cell cancer, rectal cancer, colon cancer, squamous cell lung cancer, thyroid cancer, bladder cancer, melanoma, cervical cancer, prostate cancer, breast cancer, uterine/endometrial cancer, pancreatic cancer, lung adenocarcinoma, ovarian cancer, and papillary kidney cancer.

24. The kit of claim 19, wherein the cancer is an advanced or metastatic solid tumor.

* * * * *